United States Patent
Hart et al.

(10) Patent No.: US 12,300,385 B2
(45) Date of Patent: May 13, 2025

(54) AUTOMATED DISEASE IDENTIFICATION BASED ON OPHTHALMIC IMAGES

(71) Applicant: Welch Allyn, Inc., Skaneateles Falls, NY (US)

(72) Inventors: Allen R. Hart, Knoxville, TN (US); Hongying Krause, Cranleigh (GB)

(73) Assignee: Welch Allyn, Inc., Skaneateles Falls, NY (US)

(*) Notice: Subject to any disclaimer, the term of this patent is extended or adjusted under 35 U.S.C. 154(b) by 479 days.

(21) Appl. No.: 17/709,950

(22) Filed: Mar. 31, 2022

(65) Prior Publication Data

US 2022/0319708 A1   Oct. 6, 2022

Related U.S. Application Data

(60) Provisional application No. 63/168,873, filed on Mar. 31, 2021.

(51) Int. Cl.
*G16H 50/20* (2018.01)
*G06T 7/00* (2017.01)

(52) U.S. Cl.
CPC ........... *G16H 50/20* (2018.01); *G06T 7/0012* (2013.01); *G06T 2207/30041* (2013.01)

(58) Field of Classification Search
CPC ........ G16H 50/20; G16H 30/40; G16H 50/70; G06T 7/0012; G06T 2207/30041; G06T 2207/10024; G06T 2207/10064; G06T 2207/10101; G06T 2207/20081; G06T 2207/20084

See application file for complete search history.

(56) References Cited

U.S. PATENT DOCUMENTS

| | | |
|---|---|---|
| 9,898,659 B2 | 2/2018 | Kanagasingam et al. |
| 10,468,142 B1 * | 11/2019 | Abou Shousha ...... G16H 30/20 |
| 10,599,984 B1 | 3/2020 | Wubbels et al. |
| 10,722,180 B2 | 7/2020 | Zhang et al. |

(Continued)

FOREIGN PATENT DOCUMENTS

| | | |
|---|---|---|
| AU | 2020100868 A4 | 8/2020 |
| CN | 110598836 A | 12/2019 |

(Continued)

OTHER PUBLICATIONS

Antal, B. and Hajdu, A., 2014. An ensemble-based system for automatic screening of diabetic retinopathy. Knowledge-based systems, 60, pp. 20-27.*

(Continued)

*Primary Examiner* — Zhitong Chen
(74) *Attorney, Agent, or Firm* — Lee & Hayes, P.C.

(57) ABSTRACT

An example method includes identifying at least one image of an eye of a patient. The method further includes detecting, by a first computing model, at least one first feature in the at least one image and detecting, by a second computing model, at least one second feature in the at least one image. Further, using a third computing model that is different than the first computing model or the second computing model, the method includes identifying a likelihood that the patient has one or more diseases consistent with the at least one feature and the at least one second feature. A recommendation for care of the patient is generated based on the likelihood.

23 Claims, 8 Drawing Sheets

(56) References Cited

U.S. PATENT DOCUMENTS

| | | | |
|---|---|---|---|
| 2016/0092721 A1* | 3/2016 | Kanagasingam | .... G06V 40/193 348/78 |
| 2019/0313895 A1 | 10/2019 | Hayashi et al. | |
| 2020/0187775 A1 | 6/2020 | Oh et al. | |
| 2020/0202529 A1 | 6/2020 | Hart et al. | |
| 2020/0388383 A1 | 12/2020 | Lane et al. | |

FOREIGN PATENT DOCUMENTS

| | | |
|---|---|---|
| JP | 2018027273 A | 2/2018 |
| WO | WO2019193362 A2 | 10/2019 |
| WO | WO2020186222 A1 | 9/2020 |

OTHER PUBLICATIONS

Abramoff et al., "Automated and Computer-Assisted Detection, Classification, and Diagnosis of Diabetic Retinopathy," Telemedicine and e-Health, Mary Ann Liberts, Inc., vol. 26, No. 4, Apr. 2020, pp. 544-550.

Padhy, et al., "Artificial intelligence in diabetic retinopathy: A natural step to the future," Indian Journal of Ophthalmology, vol. 67, Issue, 7, Jun. 2019, pp. 1004-1009.

\* cited by examiner

AUTOMATED DISEASE IDENTIFICATION BASED ON OPHTHALMIC IMAGES

CROSS-REFERENCE TO RELATED APPLICATION

This application is a Nonprovisional of, and claims the benefit of, U.S. Provisional Application No. 63/168,873, which was filed on Mar. 31, 2021, and is incorporated by reference herein in its entirety.

TECHNICAL FIELD

This application relates to techniques for automatically detecting diseases based on ophthalmic images obtained from a patient, as well as for providing recommendations related to the detected diseases.

BACKGROUND

Diabetes Retinopathy (DR) is a major cause for blindness worldwide. In addition, there are a few other prevalent eye diseases such as cataract (the leading cause of blindness, responsible for 51% of world blindness), glaucoma (accounts for more than 12% of all global blindness) and Age-related Macular Degeneration (AMD). Globally, AMD ranks third as a cause of blindness after cataract and glaucoma. AMD is the primary cause for blindness in industrialized countries. Various ophthalmic diseases present with abnormalities in the fundus and/or retina, such as Diabetic Macula Edema (DME), Retinal Vein Occlusion (RVO), Retinopathy of Prematurity (ROP). In addition, some systemic diseases are associated with characteristics of ophthalmic images, such as coronary microvascular dysfunction, hypertensive retinopathy, ischemic optic neuropathy, papilledema related to idiopathic intracranial hypertension, central or branch retinal artery occlusion, carotid artery occlusion, human immunodeficiency virus (HIV), acute leukemia, subacute bacterial endocarditis, sepsis, and severe anemia.

Evaluation of the retina can provide information regarding the presence and severity of many eye and systemic diseases. Although many retinal findings are sometimes non-exclusive to a particular disease, early recognition of these signs can help prevent ophthalmologic complications, vision loss as well as life threatening conditions such as stoke caused by carotid artery occlusion. Many ophthalmic and systemic diseases manifested in the retina share similar, sometimes even identical, signs with the only difference being which combinations of signs are present, varying in their morphological characteristics, distributions, location, size, and comorbidities.

SUMMARY

Various implementations of the present disclosure relate to systems, devices, and methods for identifying diseases based on ocular images. In some cases, multiple machine learning (ML) models are configured to detect different features in an ophthalmic image obtained from a patient. A further model is configured to determine one or more diseases that are depicted by the ophthalmic image based on the detected features. The one or more diseases can include ophthalmic diseases as well as systemic diseases.

Some previous technologies include using ML models to detect ophthalmic diseases based on ophthalmic images. However, these technologies use global image-based (e.g., end-to-end) ML models: that is, the images are input into the ML models and the ML models directly indicate the presence of disease in the images. Numerous training images are used to prepare these global image-based ML models, wherein the presence or absence of the disease is specifically identified using expert graders and noted with respect to each of the training images. It can be challenging to optimize global image-based ML models, particularly those designed to identify diseases that rarely materialize in a patient population, where it may be difficult to obtain sufficient training images.

In contrast to global image-based ML models, various implementations described herein include ML models configured to identify features correlated to various ophthalmic and/or systemic diseases. A single feature, such as hemorrhage, may correspond to multiple different diseases. In various cases, an evaluator is configured to determine whether ophthalmic images detect one or more diseases based on the features detected in the ocular images. In some cases, the evaluator may determine that a single ophthalmic image, patient, and/or eye, that depicts more than one disease. According to some examples, the evaluator also considers other data about the patients from which the ocular images are obtained, when determining whether the patients may be exhibiting a disease. For instance, the evaluator can additionally consider health and/or demographic-related data from an electronic medical record (EMR) of the patients.

Various implementations described herein provide a number of advantages over global image-based ML models. In some implementations, a single trained ML model may identify a type of feature correlated to multiple types of diseases, and thus can be used to identify multiple different types of diseases. In addition, training images with portions depicting a single feature that is a sign of a rare disease may be easier to obtain than whole training images that depict the rare disease. Accordingly, it may be easier and more efficient to train various ML models described herein than global image-based ML models. Furthermore, global image-based ML models are designed to identify diseases based on a single set of diagnostic rules, but different regions or practice areas may apply different types of diagnostic rules. In some implementations of the present disclosure, different diagnostic rules can be applied for classifying diseases by modifying the evaluator, rather than retraining the ML models used to identify the features. Thus, various implementations described herein are more easily adapted for different regions, changes in best practices, and other variations in care throughout different environments.

DESCRIPTION OF THE FIGURES

The following figures, which form a part of this disclosure, are illustrative of described technology and are not meant to limit the scope of the claims in any manner.

DETAILED DESCRIPTION

Figure 1:
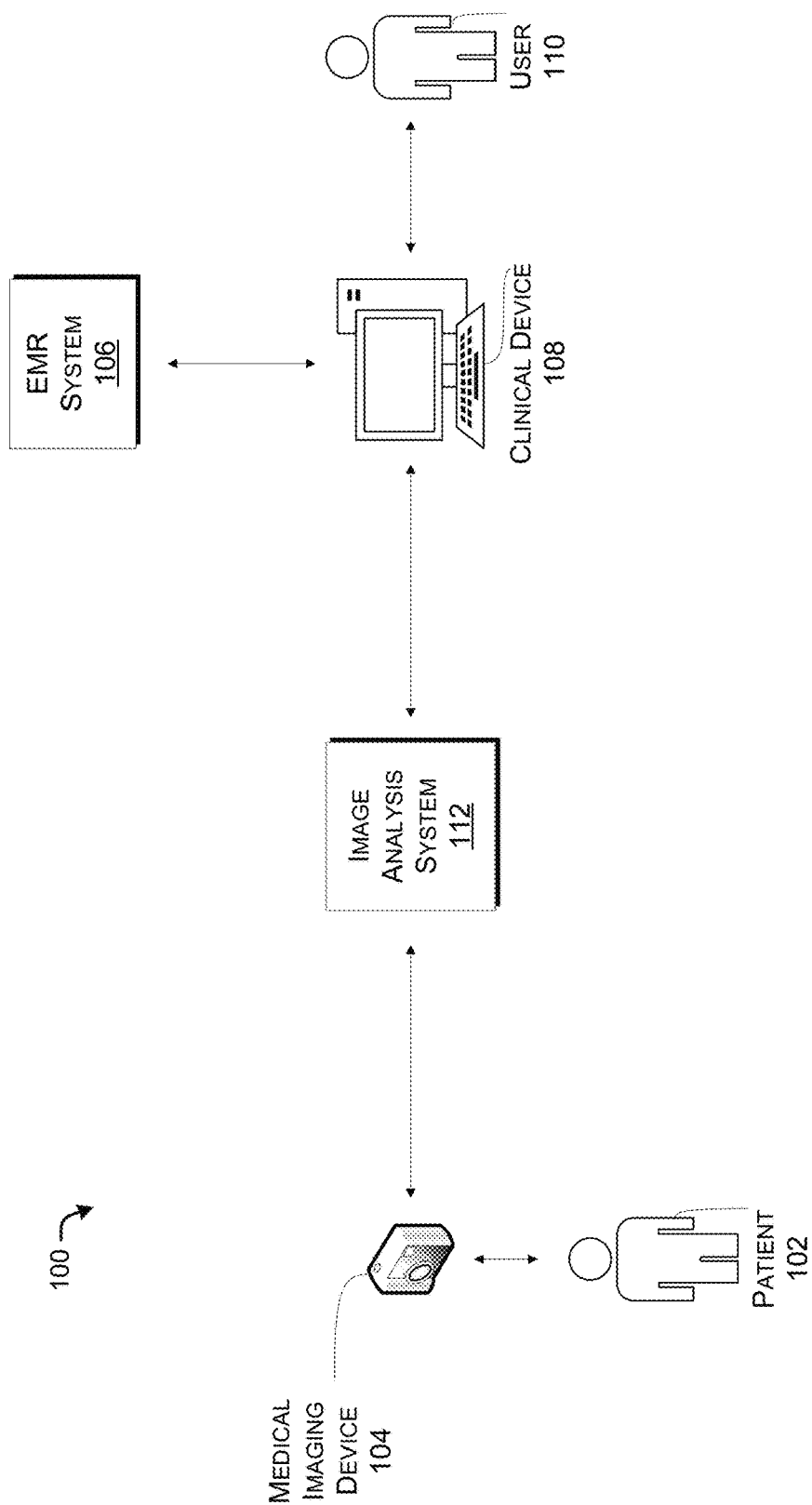
FIG. 1 illustrates an example environment for identifying one or more diseases that may be exhibited by a patient.

Various implementations of the present disclosure will be described in detail with reference to the drawings, wherein like reference numerals present like parts and assemblies throughout the several views. Additionally, any samples set forth in this specification are not intended to be limiting and merely set forth some of the many possible implementations.

FIG. 1 illustrates an example environment 100 for identifying one or more diseases that may be exhibited by a patient 102. The patient 102 may be any individual with eyes, such as a human monitored in a clinical environment or a person presenting for a medical appointment.

A medical imaging device 104 is configured to obtain one or more images of at least one eye of the patient 102. In various implementations, the medical imaging device 104 includes an optical coherence tomography (OCT) camera configured to obtain OCT images of the eye(s) of the patient 102. In some cases, the medical imaging device 104 includes a slit lamp imaging device configured to obtain slit lamp images (or projection images) of the eye(s) of the patient 102. In particular cases, the medical imaging device 104 may include at least one fluorescence camera configured to obtain one or more fluorescence angiograms of the eye(s) of the patient 102. In some examples, the medical imaging device 104 may be configured to generate one or more color fundus (e.g., retinal) photography (CFP) images of the eye(s) of the patient 102, one or more fluorescein angiography (FA) images of the eye(s) of the patient 102, one or more indocyanine green (ICG) angiography images of the eye(s) of the patient 102, one or more fundus autofluorescence (FAF) images of the patient, or any combination thereof. For example, the medical imaging device 104 is configured to obtain images of at least one retina of the patient 102 and/or at least one fundus of the patient 102.

In addition, an electronic medical record (EMR) system 106 may be configured to store data indicative of the patient 102. As used herein, the terms "electronic health record," "electronic medical record," "EMR," and their equivalents, may refer to a collection of stored data indicative of a medical history and/or at least one medical condition of an individual, wherein the stored data is accessible (e.g., can be modified and/or retrieved) by one or more computing devices. An EMR of an individual may include data indicating previous or current medical conditions, diagnostic tests, or treatments of the individual. For instance, the EMR may indicate demographics of the individual, parameters (e.g., vital signs) of the individual, notes from one or more medical appointments attended by the individual, medications prescribed or administered to the individual, therapies (e.g., surgeries, outpatient procedures, etc.) administered to the individual, results of diagnostic tests performed on the individual, identifying information (e.g., a name, birthdate, etc.) of the individual, or a combination thereof. In some examples, the EMR system 106 may be implemented on one or more servers, such as servers located in at least one data center.

The EMR system 106 may be connected to a clinical device 108, which may be operated by a user 110. The clinical device 108 can include a computing device, such as a device including at least one processor configured to perform operations. In some cases, the operations are stored in memory in an executable format. Examples of computing devices include a personal computer, a tablet computer, a smart television (TV), a mobile device, a mobile phone, or an Internet of Things (IoT) device.

In various implementations, the user 110 may be different than the patient 102. In some cases, the user 110 is a care provider. For example, the user 110 is a clinician, such as a nurse, a physician, a physician's assistant (PA), a medical student, a nursing student, or a medical technician.

The medical imaging device 104 and the clinical device 108 may be connected to an imaging analysis system 112. The imaging analysis 112 may be implemented by one or more computing devices, such as a device including a processor configured to perform various operations stored in memory. In various implementations, the imaging analysis system 112 may receive the image(s) from the medical imaging device 104, receive the EMR data from the EMR system 106, and determine whether the patient 102 is exhibiting one or more diseases based on the image(s) and/or the EMR data. In some cases, the imaging analysis system 112 receives the EMR data from the EMR system 106 via the clinical device 108. In some cases, the EMR system 106 transmits the EMR data to the imaging analysis system 112 through a communication path that omits the clinical device 108.

In various examples, the imaging analysis system 112 is configured to confirm an image quality of the image(s) received from the medical imaging device 104. As used herein, the term "image quality," and its equivalents, may refer to an extent to which an image accurately represents a subject depicted in the image. Several factors may be associated with image quality, such as a blurriness of the image or other distortions in the image. In some examples in which a quality of the image(s) is determined to be below a threshold, the imaging analysis system 112 may refrain from analyzing the image(s) and/or generate a notification indicating that the image(s) are of an insufficient quality. The imaging analysis system 112 may transmit the notification to the medical imaging device 104, which may retake the image(s) from the patient 102 based on the notification. In some examples, the imaging analysis system 112 transmits the notification to the clinical device 108, which may output a request to retake the image(s) to the user 110. In various examples in which the medical imaging analysis system 112 confirms that the image(s) are of a sufficient quality, the imaging analysis system 112 performs further analysis on the image(s).

According to some implementations, the imaging analysis system 112 includes multiple computing models that the imaging analysis system 112 uses to respectively detect different types of features in the image(s). As used herein, the term "feature," and its equivalents, may refer to a structure or visible sign within an image of an eye that may be correlated with one or more diseases and/or medical conditions. Examples of features include at least one of a microaneurysm, a hemorrhage, drusen, exudate, edema, a cup/disc ratio (CDR), focal arteriolar narrowing, arteriovenous nicking, a cotton wool spot, an embolus, a red spot, retinal whitening, a Hollenhorst plaque, a Roth spot, a microinfarct, coagulated fibrin, new vessels elsewhere (NVE), a vitreous hemorrhage (VH), a pre-retinal hemorrhage (PRH), new vessels on a disc (NVD), venous beading, or an intraretinal microvascular abnormality (IRMA). In some cases, the imaging analysis system 112 uses an example computing model to identify the presence of a type of feature in the image(s), a location of the type of feature in the image(s) (e.g., what quadrant of an eye includes an identified feature), a size of the type of feature in the image(s), or any combination thereof. According to some cases, the imaging analysis system 112 uses at least one of the computing models to identify a landmark in the image(s). As used herein, the term "landmark," and its equivalents, may refer to an anatomical structure that is observed in healthy and diseased eyes. Examples of landmarks include comprising at least one of a macula, an optic disc (OD), a retina, a cornea, an iris, a lens, one or more retinal layers, one or more vessels, or a fovea. In various examples, the imaging analysis system 112 uses an example computing model to identify a proximity (e.g., a distance) between one or more landmarks and a detected feature in an eye of the patient 102.

In some cases, the computing models include machine learning (ML) models. As used herein, the terms "machine learning," "ML," and their equivalents, may refer to a computing model that can be optimized to accurately recreate certain outputs based on certain inputs. In some examples, the ML models include deep learning models, such as convolutional neural networks (CNN), image transformers, any combination thereof, or other types of NNs. The term Neural Network (NN), and its equivalents, may refer to a model with multiple hidden layers, wherein the model receives an input (e.g., at least one vector, matrix, or tensor) and transforms the input by performing operations via the hidden layers. An individual hidden layer may include multiple "neurons," each of which may be disconnected from other neurons in the layer. An individual neuron within a particular layer may be connected to multiple (e.g., all) of the neurons in the previous layer, based on the model architecture. In some examples, a NN may further include at least one fully-connected layer that receives a feature map output by the hidden layers and transforms the feature map into the output of the NN. The output of an NN can be in any form based on the purpose of the learning network. For example, the output can be a name of a detected feature, a location of the detected feature, an indication of the presence of the detected feature, or any combination thereof.

As used herein, the term "CNN," and its equivalents and variants, may refer to a type of NN model that performs at least one convolution (or cross correlation) operation on an input image and may generate an output image based on the convolved (or cross-correlated) input image. A CNN may include multiple layers that transforms an input image (e.g., an ophthalmic image) into an output image via a convolutional or cross-correlative model defined according to one or more parameters. The parameters of a given layer may correspond to one or more filters, which may be digital image filters that can be represented as images (e.g., 2D images). A filter in a layer may correspond to a neuron in the layer. A layer in the CNN may convolve or cross correlate its corresponding filter(s) with the input image in order to generate the output image. In various examples, a neuron in a layer of the CNN may be connected to a subset of neurons in a previous layer of the CNN, such that the neuron may receive an input from the subset of neurons in the previous layer, and may output at least a portion of an output image by performing an operation (e.g., a dot product, convolution, cross-correlation, or the like) on the input from the subset of neurons in the previous layer. The subset of neurons in the previous layer may be defined according to a "receptive field" of the neuron, which may also correspond to the filter size of the neuron. U-Net (see, e.g., Ronneberger, et al., arXiv:1505.04597v1, 2015) is an example of a CNN model.

The ML models of the imaging analysis system 112 may be pre-trained based on training images that depict the features, as well as indications that the training images depict the features. For example, one or more expert graders may review the training images and indicate whether they identify the features in the training images. Data indicative of the training images, as well as the gradings by the expert grader(s), may be used to train the ML models. The ML models may be therefore trained to identify the features in the image(s) obtained from the patient 102. Implementations related to the computing models that detect features in the image(s) will be described in further detail with respect to FIGS. 2-3.

Other types of NN frameworks can also be used. For example, the imaging analysis system 112 may include one or more transformer based models, such as ViT (Dosovitskiy et al., arXiv:2010.11929v2, 3 Jun. 2021) and/or Swin Transformer (Liu et al., arXiv:2111.09883v1, 18 Nov. 2021). For instance, a transformer-based model can be used as backbones for NNs of the imaging analysis system 112.

In various examples, the imaging analysis system 112 may be configured to identify whether the patient 102 is exhibiting one or more diseases based on the identified features. As used herein, the term "disease," and its equivalents, refers to a pathology. Examples of diseases that can be identified by the imaging analysis system 112 include at least one of diabetic retinopathy (DR), age-related macular degeneration (AMD), diabetic macula edema (DME), retinal vein occlusion (RVO), retinopathy of prematurity (ROP), coronary microvascular dysfunction, hypertensive retinopathy, ischemic optic neuropathy, papilledema, retinal artery occlusion, carotid artery occlusion, human immunodeficiency virus (HIV), acquired immunodeficiency syndrome (AIDS), syphilis, malaria, chicken pox, Lyme disease, leukemia, subacute bacterial endocarditis, sepsis, or anemia. In some examples, the imaging analysis system 112 includes a computing model (e.g., a ML model, a look-up table, etc.) that the imaging analysis system 112 uses to identify the disease(s). For example, the computing model may include correlations between identified features and multiple diseases. In some cases, the diseases that are identifiable by the imaging analysis system 112 include both ophthalmic and systemic diseases. In some cases, the computing model identifies likelihoods that the image(s) depict respective diseases.

In some cases, there are different ways of defining a disease based on the identified features. For example, standard of practice in one geographic region (e.g., the United States) might be to identify certain features as indicative of a particular disease, whereas standard of practice in another geographic region (e.g., the United Kingdom) might be to identify different features as indicative of the particular disease. That is, there may be different standards of practice corresponding to correlations between features and the particular disease. In various implementations, the imaging analysis system 112 may determine whether the patient 102 is exhibiting a disease according to multiple standards of practice. In some cases, the user 110 may indicate a particular standard of practice, and the imaging analysis system 112 may determine whether the patient 102 is exhibiting various diseases in accordance with the indicated standard of practice. Further implementations of features related to identifying diseases will be described below with reference to FIG. 5.

In various implementations, the imaging analysis system 112 may generate a recommendation based on one or more diseases of the patient 102. In some examples, the imaging analysis system 112 transmits the recommendation to the clinical device 108. The recommendation may be output to the user 110 by the clinical device 108. Accordingly, the user 110 may take various actions to further diagnose and/or treat the patient 102 for any diseases identified by the image analysis system 112. In some examples, the image analysis system 112 may transmit the recommendation to the EMR system 106, which may store data indicative of the recommendation in the EMR of the patient 102. Accordingly, the recommendation may be accessed by other users caring for the patient 102 in the future.

Although FIG. 1 illustrates the medical imaging device 104, the EMR system 106, the clinical device 108, and the image analysis system 112 as separate entities, implementations are not so limited. For example, one or more of the medical imaging device 104, the EMR system 106, the clinical device, or the image analysis system 112 may be implemented by the same computing device.

Although not explicitly shown in FIG. 1, various elements illustrated in FIG. 1 may be connected by one or more communication networks. For instance, any of the arrows illustrated in FIG. 1 may represent one or more communication interfaces traversing the communication network(s). Examples of communication networks include at least one wired interface (e.g., an ethernet interface, an optical cable interface, etc.) and/or at least one wireless interface (e.g., a BLUETOOTH interface, a WI-FI interface, a near-field communication (NFC) interface, a Long Term Evolution (LTE) interface, a New Radio (NR) interface, etc.). In some cases, data or other signals are transmitted between elements of FIG. 1 over a wide area network (WAN), such as the Internet. In some cases, the data include one or more data packets (e.g., Internet Protocol (IP) data packets), datagrams, or a combination thereof.

Figure 2:
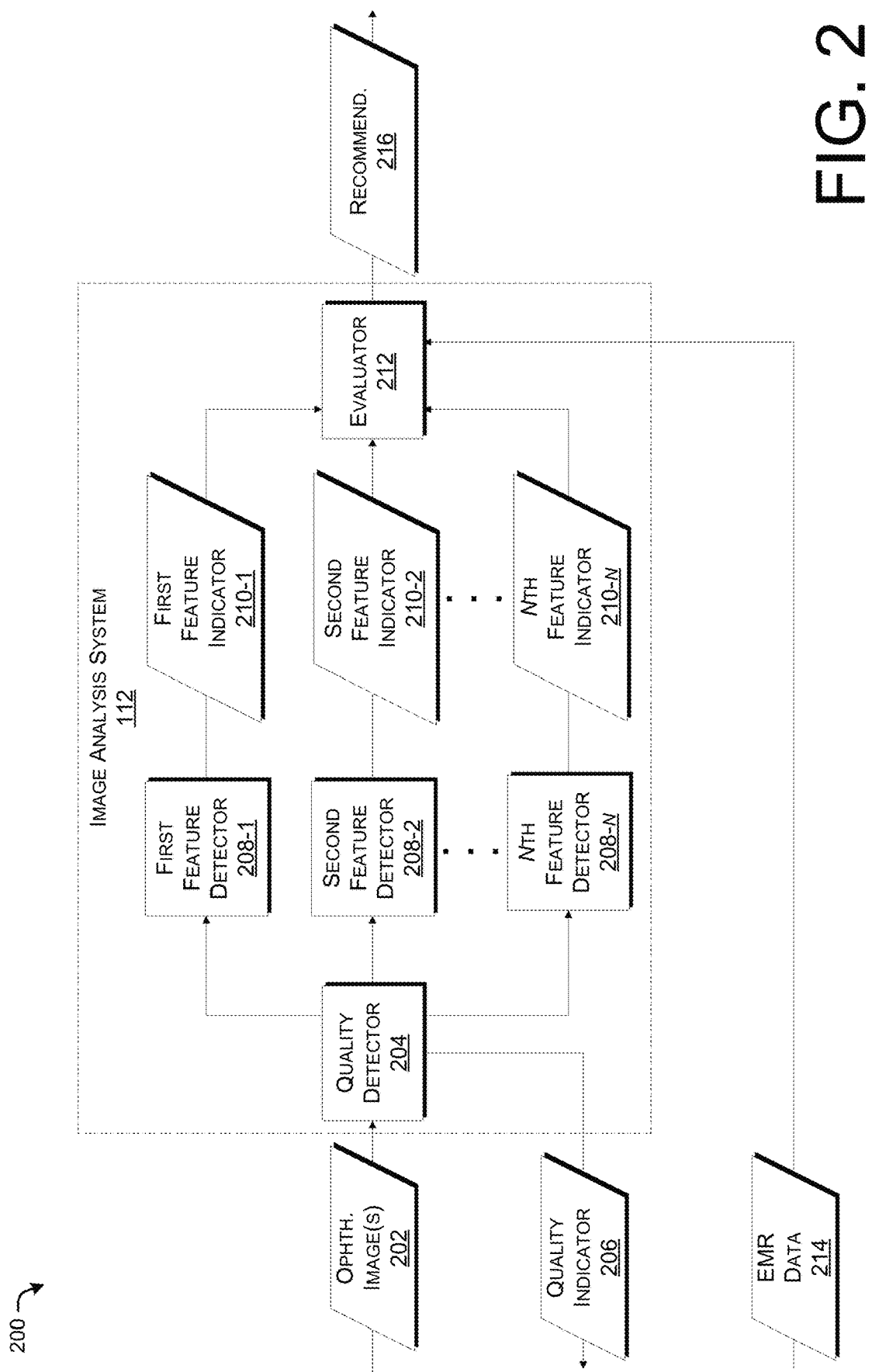
FIG. 2 illustrates an example environment for analyzing at least one image of an eye of a patient.

FIG. 2 illustrates an example environment 200 for analyzing at least one image of an eye of a patient. As illustrated, the environment 200 includes the image analysis system 112 described above with reference to FIG. 1. In particular, the image analysis system 112 receives and/or identifies one or more ophthalmic images 202. The ophthalmic image(s) 202 depict at least one eye of a patient, such as the patient 102 described above with reference to FIG. 1. For example, the ophthalmic image(s) 202 include at least one OCT image and/or slit lamp image of an eye of the patient. In some examples, the ophthalmic image(s) depict a retina and/or fundus of the patient.

The image analysis system 112 includes a quality detector 204 that is configured to assess a quality of the ophthalmic image(s) 202. For example, the quality detector 204 may identify a quality of the ophthalmic image(s) 202 based on a blurriness of the ophthalmic image(s) 202, blocking in the ophthalmic image(s) 202, ringing in the ophthalmic image(s) 202, image sharpness of the ophthalmic image(s) 202, noise (e.g., white noise) in the ophthalmic image(s) 202, dynamic range of the ophthalmic image(s) 202, contrast in the ophthalmic image(s) 202, color in the ophthalmic image(s) 202, distortion in the ophthalmic image(s) 202, vignetting in the ophthalmic image(s) 202, lateral chromatic aberration (LCA) in the ophthalmic image(s) 202, artifacts in the ophthalmic image(s) 202, any other qualities that impact the accuracy of ophthalmic structures depicted in the ophthalmic image(s) 202, or any combination thereof. For instance, the quality detector 204 may perform an objective, no-reference technique for identifying the image quality of ophthalmic image(s) 202. In some examples, the quality detector 204 generates a quality indicator 206 that indicates the quality of the ophthalmic image(s) 202. In some cases, the quality detector 204 compares the quality of the ophthalmic image(s) 202 to a threshold and indicates the comparison in the quality indicator 206. For instance, the quality detector 204 may indicate that the quality of the ophthalmic image(s) 202 is below the threshold, which may indicate that any further analysis on the ophthalmic image(s) 202 could be inaccurate or unreliable.

In some implementations, the quality detector 204 determines that the ophthalmic image(s) 202 are of a sufficient quality for further processing. For instance, the quality detector 204 may determine that the quality of the ophthalmic image(s) 202 is greater than or equal to the threshold. In various implementations, the quality detector 204 may provide the ophthalmic image(s) 202 to first to nth feature detectors 208-1 to 208-$n$ based on determining that the ophthalmic image(s) 202 are of sufficient quality for further processing.

The first to nth feature detectors 208-1 to 208-$n$ may be configured to identify first to nth features in the ophthalmic image(s) 202, wherein n is an integer greater than 1. That is, the first feature detector 208-1 may identify a first feature in the ophthalmic image(s) 202, the second feature detector 208-2 may identify a second feature in the ophthalmic image(s) 202, and the nth feature detector 208-$n$ may identify an nth feature in the ophthalmic image(s) 202. In various examples, a single feature detected by one of the first to nth feature detectors 208-1 to 208-$n$ is associated with multiple different diseases. In some cases, the first to nth feature detectors 208-1 to 208-$n$ are configured to identify a presence or absence of the multiple features. In some implementations, the first to nth feature detectors 208-1 to 208-$n$ are configured to identify sizes and/or shapes of the features in the ophthalmic image(s) 202 and/or the eye(s) depicted in the ophthalmic image(s) 202. In some cases, the first to nth feature detectors are configured to identify locations of the features in the ophthalmic image(s) 202 and/or the eye(s) depicted in the ophthalmic image(s) 202. As shown, the first to nth feature detectors 208-1 to 208-$n$ are arranged in parallel, and may analyze the ophthalmic image(s) 202 independently of one another.

In various examples, at least one of the first to nth feature detectors 208-1 to 208-$n$ is configured to detect one or more landmarks in the ophthalmic image(s) 202. The landmark(s) may include at least one of a macula, an OD, a retina, a cornea, an iris, a lens, one or more retinal layers, vessels or a fovea. According to some cases, at least one of the first to nth feature detectors 208-1 to 208-$n$ may be further configured to identify a proximity (e.g., a distance) between an identified feature and an identified landmark within the ophthalmic image(s) 202 and/or the eye(s) depicted in the ophthalmic image(s) 202.

According to some examples, the first to nth feature detectors 208-1 to 208-$n$ include computing models that are used to identify the features. In some cases, the computing models include ML models, such as one or more CNNs based models, transformer-based models, other types of models, or any combination thereof. In particular examples, the ML models of the respective first to nth feature detectors 208-1 to 208-$n$ are trained separately. For example, a first set of images can be used to train the first feature detector 208-1 and a second set of images can be used to train the second feature detector 208-2, wherein the first set of images are different than the second set of images.

The first to nth feature detectors 208-1 to 208-n respectively generate first to nth feature indicators 210-1 to 210-n. The first to nth feature indicators 210-1 to 210-n may indicate the presence and/or absence of the first to nth features, the number of any of the first to nth features, the size and/or shape of any of the first to nth features, the location of any of the first to nth features, the proximity of any of the first to nth features to landmarks, and so on, within the ophthalmic image(s) 202 and/or the eyes depicted in the ophthalmic image(s) 202.

The first to nth feature detectors 208-1 to 208-n may provide the first to nth feature indicators 210-1 to 210-n to an evaluator 212. The evaluator 212 may be configured to identify whether the ophthalmic image(s) 202 depict one or more diseases and/or a disease severity based on the first to nth feature indicators 210-1 to 210-n. Examples of the disease(s) that the evaluator 212 may identify in the ophthalmic image(s) 202 include at least one of diabetic retinopathy (DR), age-related macular degeneration (AMD), diabetic macula edema (DME), retinal vein occlusion (RVO), retinopathy of prematurity (ROP), coronary microvascular dysfunction, hypertensive retinopathy, ischemic optic neuropathy, papilledema, retinal artery occlusion, carotid artery occlusion, human immunodeficiency virus (HIV), acquired immunodeficiency syndrome (AIDS), syphilis, malaria, chicken pox, Lyme disease, leukemia, subacute bacterial endocarditis, sepsis, or anemia. The evaluator 212 may include a computing model (e.g., a look-up table, a ML model, etc.) configured to identify at least one disease in the ophthalmic image(s) 202.

In some examples, the evaluator 212 may further receive EMR data 214 that is indicative of data stored in an EMR of the patient depicted in the ophthalmic image(s) 202. In some cases, the evaluator 212 may identify at least one disease in the ophthalmic image(s) 202 and/or a disease severity based, at least in part, on the EMR data 214. For example, the evaluator 212 may distinguish between sepsis and severe anemia based on indications in the EMR data 214 of a medical history of surgical procedures, implants, excessive bleeding, etc.

The evaluator 212 may generate a recommendation 216 based on any disease identified in the ophthalmic image(s) 202. In some cases, the recommendation 216 may indicate the identified disease(s). In some examples, the evaluator 212 may determine, based on the identified disease(s) and using a look-up table or other computing model, whether a referral to a specialist is warranted and/or a therapy that treats the identified disease(s). The recommendation 216 may include whether the referral is warranted and/or any applicable therapy.

Specific examples for comprehensive disease identification will now be described with reference to FIG. 2. In some implementations, the environment 200 may be used to identify different types of maculopathy in the ophthalmic image(s) 202. Possible maculopathies include DME, DR, and AMD. For instance, there are a number of features that may distinguish DME, DR, and AMD for the purposes of disease classification. DME may include more exudate than hemorrhage. Proliferative DR may be similar to retinal occlusion. Size may matter: for example, if a bleed is observed underneath a retina, there may be a relatively large blood hemorrhage.

AMD, for instance, may be associated with a larger hemorrhage than DME. As dry AMD progresses and becomes worse, then it may be considered wet AMD. The progression of dry to wet AMD may be associated with certain features. For instance, drusen itself may not be indicative of progression, but changes in hemorrhage and/or pigment may indicate progression of dry to wet AMD. Dry AMD may have no hemorrhage, exudate, or edema, whereas wet AMD may have edema and/or hemorrhage. In some implementations, the image analysis system 112 may determine that the patient is exhibiting a progression to wet AMD based on a fluorescence angiogram.

DME may exhibit different features than AMD. For example, DME may correspond to small (e.g., dot) hemorrhages. In some cases, DME may also be associated with clusters of hemorrhage. MAs and exudate may also be associated with DME. However, after treatment (e.g., several months of treatment), the exudate may be reduced. DME may be associated with exudate that appears close to MA. In some examples, if there is drusen and exudate, but no MA, AMD may be indicated rather than DME.

The following Table 1 illustrates different types of features that are associated with DME and AMD as well as how DME and AMD are distinguishable from one another:

TABLE 1

| Disease | Features |
|---------|----------|
| DME | Greater exudate than hemorrhage, small hemorrhage, exudate close to MA |
| AMD | Drusen, exudate, no MA, large hemorrhage |

The image analysis system 112 may be configured to identify DME or AMD in the ophthalmic image(s) 202 by including a first feature detector 208-1 configured to identify the presence, amount, and location of exudate in the ophthalmic image(s) 202; a second feature detector 208-2 configured to identify the presence of hemorrhage and amount of hemorrhage in the ophthalmic image(s) 202; a third feature detector 208-3 configured to identify the presence of drusen in the ophthalmic image(s) 202; and a fourth feature detector 208-4 configured to identify the presence and location of MA in the ophthalmic image(s) 202. The evaluator 212 may receive the identifications of the first through fourth feature detectors 208-1 to 208-4 and determine a likelihood that the patient is exhibiting DME and/or a likelihood that the patient is exhibiting AMD.

Further, in some examples, the evaluator 212 may identify a treatment for the patient based on the likelihood that the patient is exhibiting DME and/or the likelihood that the patient is exhibiting AMD. If the likelihood of DME is greater than a threshold (e.g., 50%, 70%, or the like), the evaluator 212 may generate the recommendation 216 to indicate that the patient can be treated with internal injection of an anti-vascular endothelial growth factor (anti-VEGF) agent, such as ranibizumab or aflibercept, or another medicine such as ozudex dexamethasone. In some cases, the evaluator 212 may generate the recommendation 216 to indicate that the patient is to be treated with a diet that reduces blood pressure, lipids, and blood sugar to reduce the risk of complications of the DME. Further, the evaluator 212 may identify one or more referrals and/or additional diagnostic steps based on the likelihood of DME. For example, since individuals with DME have a heightened risk of kidney disease, the evaluator 212 may generate the recommendation 216 with a referral to a kidney specialist. In some cases, the evaluator 212 may generate the recommendation 216 to indicate that tests for hemoglobin subunit alpha 1

(HBA1) and hemoglobin subunit alpha 2 (HBA2) levels should be performed to monitor DME progression.

In some implementations, the system 200 may be used to identify RVO within the ophthalmic image(s) 202. In particular, RVO may present similarly to DME, but is different than DME based on the positions of hemorrhages. For example, Table 2 illustrates examples of features associated with DME and RVO, and how those diseases can be distinguished from one another.

TABLE 2

| Disease | Features |
| --- | --- |
| DME | Greater exudate than hemorrhage, small hemorrhage, exudate close to MA |
| RVO | Hemorrhage near middle retina, exudate near nerve, and hemorrhage forms arching shape |

The image analysis system 112 may be configured to identify DME or RVO in the ophthalmic image(s) 202 by including a first feature detector 208-1 configured to identify the presence, amount, and location of exudate in the ophthalmic image(s) 202; a second feature detector 208-2 configured to identify the presence, shape, and amount of hemorrhage in the ophthalmic image(s) 202; and a third feature detector 208-3 configured to identify the presence and location of MA in the ophthalmic image(s) 202. Further, the first feature detector 208-1 may be configured to identify the location of a landmark, such as a nerve in the ophthalmic image(s) 202. The second feature detector 208-2 may be configured to identify the presence of landmarks in the ophthalmic image(s) 202, such as the middle retina depicted in the ophthalmic image(s) 202, as well as the proximity of the hemorrhage to the landmarks. The evaluator 212 may receive the identifications of the first through fourth feature detectors 208-1 to 208-4 and determine a likelihood that the patient is exhibiting DME and/or a likelihood that the patient is exhibiting RVO.

In some implementations, the environment 200 may be used to identify OD abnormalities depicted in the ophthalmic image(s) 202, which may be indicative of glaucoma. Glaucoma is associated with high vertical cup/disc ratio (CDR), variable CDR between eyes, hemorrhage on OD, and wedge defect. For example, the first feature detector 208-1 may be configured to identify a first OD in a first ophthalmic image 202 of a first eye of the patient and the second feature detector 208-2 may be configured to identify a second OD in a second ophthalmic image 202 of a second eye of the patient. The first feature detector 208-1 may be configured to identify a first CDR based on the first OD, and the second feature detector 208-2 may be configured to identify a second CDR based on the second OD. Further, the third feature detector 208-3 may be configured to identify the position of hemorrhage and OD within the ophthalmic image(s) 202, and the fourth feature detector 208-4 may be configured to identify a wedge defect within the ophthalmic image(s) 202. In some cases, the evaluator 212 may generate the recommendation 216 to indicate possible glaucoma when the first CDR and/or the second CDR are greater than a first threshold, when a difference between the first CDR and/or the second CDR is greater than a second threshold (e.g., 0.2), when hemorrhage is observed on the OD, wedge defect is present, or a combination thereof.

According to some implementations, the environment 200 may be used to identify retinal abnormalities depicted in the ophthalmic image(s) 202. For example, the following Table 3 summarizes diseases and features associated with various retinal abnormalities.

TABLE 3

| Disease | Features |
| --- | --- |
| Coronary Microvascular Dysfunction | Isolated MAs and hemorrhages, focal interior narrowing, arterio-venous nicking |
| Hypertensive Retinopathy | Exudate, hemorrhage, cotton wool, arteriolar narrowing, increased arteriolar light reflexes |
| Ischemic Optic Neuropathy | OD swelling, hemorrhage, exudate, and cotton wool |
| Papilledema (related to intracranial pressure or idiopathic intra-cranial hypertension) | Retinal edema and hemorrhage and papilledema overlapping the OD; one or more changes to OD |
| Central Retinal Artery Occlusion | Abnormal vessel, emboli, red spot, whitening area, hemorrhage |
| Carotid Artery Occlusion | Emboli, Hollenhorst plaques (i.e., cholesterol emboli in blood vessels of the retina) |
| Branch Retinal Artery Occlusion | Emboli, Hollenhorst plaques (i.e., cholesterol emboli in blood vessels of the retina), whitening area |
| HIV | Cotton wool spots and distribution of cotton wool spots |
| Acute Leukemia | Presence, shape, and distribution of hemorrhage |
| Subacute Bacterial Endocarditis, Sepsis, Severe Anemia | Roth spots (i.e., a cotton wool spot surrounded by hemorrhage), hemorrhage |

The image analysis system 112 may be configured to identify any of the diseases listed above in the ophthalmic image(s) 202 by including multiple feature detectors 208 respectively detecting the potential features listed above. In various implementations, the evaluator 212 may further distinguish between diseases based on EMR data 214. For example, subacute bacterial endocarditis, sepsis, and severe anemia present with similar ophthalmic features (e.g., Roth spots). The first through nth feature indicators 210-1 to 210-n may indicate the presence of Roth spots in the ophthalmic image(s) 202 to the evaluator 212. The evaluator 212 may use the EMR data 214 to distinguish between different diseases associated with Roth spots. For example, if the EMR data 214 indicates that the patient has a history of bleeding or anemia, the evaluator 212 may increase the likelihood that a patient with Roth spots has severe anemia, rather than subacute bacterial endocarditis or sepsis. Similarly, if the EMR data 214 indicates that patient has a history of an invasive or semi-invasive procedure (e.g., a surgery, implant, feeding tube, etc.), the evaluator 212 may increase the likelihood that the patient with Roth spots has sepsis. Further, if the EMR data 214 indicates that the patient has a history of a *Streptococcus* infection and/or excessive sweating, the evaluator 212 may increase the likelihood that the patient with Roth spots has subacute bacterial endocarditis. In various implementations, the image analysis system 112 may adjust the recommendation 216 based on the EMR data 214.

In various implementations, the environment 200 may be used to evaluate disease progression or severity. For example, the image analysis system 112 may identify that the ophthalmic image(s) 202 are consistent with DR. Further, in some cases, the EMR data 214 may indicate that the patient has diabetes. In addition, the evaluator 212 may generate the recommendation 216 based on a severity of the DR. There are multiple grading schemes (e.g., standards of practice) regarding DR severity, including the Early Treatment Diabetic Retinopathy Study (ETDRS) scheme, the National Screening Committee (NSC) scheme, the Scottish Diabetic Retinopathy Grading Scheme (SDRGS), the American Academy of Ophthalmology (AAO) scheme, and the RCOphth scheme. In some examples, the evaluator 212 may generate three recommendations 216 indicating DR severity and/or progression respectively corresponding to ETDRS, ICDRS, and NSC.

The ETDRS scale and corresponding features are provided in the following Table 4:

TABLE 4

| ETDRS Level | ETDRS Severity | Features |
| --- | --- | --- |
| 10 | No apparent retinopathy | Features absent |
| 14, 15 | No apparent retinopathy | Features questionable |
| 20 | Very mild NPDR | MAs present |
| 35 | Mild NPDR | Exudates, cotton-wool spots, and/or mild retinal hemorrhages, such as: 35A: venous loops ≥ definite in one quadrant 35B: SE, IRMA, or venous beading (VB) questionable 35C: retinal hemorrhages present 35D: hard exudate (HE) ≥ definite in one quadrant 35E: soft exudate (SE) ≥ definite in one quadrant |
| 43 | Moderate NPDR | 43A: retinal hemorrhages moderate in four quadrants or severe in one quadrant 43B: mild IRMA in 1 to 3 quadrants |
| 47 | Moderate NPDR | 47A: both level 43 features 47B: mild IRMA in 4 quadrants 47C: severe retinal hemorrhage in 2 to 3 quadrants 47D venous beading in 1 quadrant |
| 53A-D | Severe NPDR | 53A: two or more level 47 features 53B: severe retinal hemorrhages in 4 quadrants 53C: moderate to severe IRMA in at least one quadrant 53D: venous beading in at least 2 quadrants |
| 53E | Very Severe NPDR | At least two level 53A-D characteristics |
| 61 | Mild PDR | NVE in less than half of OD area in 1 or more quadrants |
| 65 | Moderate PDR | 65A: NVE in greater than or equal to half of disk area in 1 or more quadrants 65B: NVD less than 0.25 to 0.33 of disk area |
| 71 and 75 | High-risk PDR | NVD is greater than or equal to 0.25 to 0.33 of disk area; NVD less than 0.25 to 0.33 of disk area; NVE greater than or equal to 0.5 of disk area plus VH or PRH, or VH or PRH obscuring greater than or equal to 1 OD area |
| 81 and 85 | Advanced PDR | Fundus partially obscured by VH and other new vessels ungradable or retina detached at center of the macula |

As used herein, the term "quadrant," and its equivalents, may refer to a fourth of the eye or a fourth of a non-fovea area of the eye. In the ETDRS system, the retina is divided into the following four quadrants: superior quadrant (which is defined above the fovea), nasal quadrant (which is defined between the fovea and the nose), inferior quadrant (which is defined below the fovea), and temporal quadrant (which is defined between the temple and the fovea). Using various implementations described herein, the first to nth feature detectors 208-1 to 208-n may respectively identify the features listed in Table 4 above. For example, the first to nth feature detectors 208-1 to 208-n may identify the following features: MAs, exudate, hemorrhage, IRMA, NVE, VH, PRH, NVD, NVE, venous beading, as well as the sizes and locations of the respective features. Further, the evaluator 212 may include a look-up table consistent with Table 4 to generate the recommendation 216 to indicate the ETDRS level and/or severity depicted in the ophthalmic image(s) 202 based on the first to nth feature indicators 210-1 to 210-n generated by the first to nth feature detectors 208-1 to 208-n.

In some cases, the evaluator 212 may further generate additional recommendations 216 associated with additional, different standards of practice beyond ETDRS. For example, the following Table 5 illustrates the relationship between ETDRS, NSC, Scottish Diabetic Retinopathy Grading System (SDRGS), AAO, and the Royal College of Ophthalmologists standard (RCOphth):

TABLE 5

| ETDRS Level | NSC Level | SDRGS Level | AAO Level | RCOphth Level |
| --- | --- | --- | --- | --- |
| 10 | R0 none | R0 none | No apparent retinopathy | None |
| 20 | R1 | R1 mild background | Mild NPDR | Low risk |
| 35 | R1 | R1 mild background | Mod NPDR | Low risk |
| 43 | R2 preproliferative | R2 moderate BDR | Mod NPDR | High risk |
| 47 | R2 preproliferative | R2 moderate BDR | Mod NPDR | High risk |
| 53A-D | R2 preproliferative | R3 severe BDR | Severe NPDR | High risk |
| 53E | R2 preproliferative | R3 severe BDR | Severe NPDR | High risk |
| 61 | R3 proliferative | R4 PDR | PDR | PDR |
| 65 | R3 proliferative | R4 PDR | PDR | PDR |
| 71, 75 | R3 proliferative | R4 PDR | PDR | PDR |
| 81, 85 | R3 proliferative | R4 PDR | PDR | PDR |

In various implementations, the evaluator 212 may be configured to generate multiple recommendations 216 corresponding respectively to multiple standards of practice associated with two or more of ETDRS, NSC, SDRGS, AAO, and RCOphth. For example, the evaluator 212 may include a look-up table consistent with Table 5 that indicates correlations between ETDRS levels and/or the features of ETDRS with NSC, SDRGS, AAO, and RCOphth. In some cases, a user may indicate a particular standard of practice among ETDRS, NSC, SDRGS, AAO, and RCOphth, and the evaluator 212 may generate the recommendation 216 in accordance with the indicated standard of practice. In various implementations, the evaluator 212 may be configured to identify DR severity in accordance with multiple standards of practice without including a ML model that is trained in accordance with a single standard of practice. Rather, the features identified by any ML models included in the first to nth feature detectors 208-1 to 208-n may be applicable to multiple different standards of practice considered by the evaluator 212.

Figure 3:
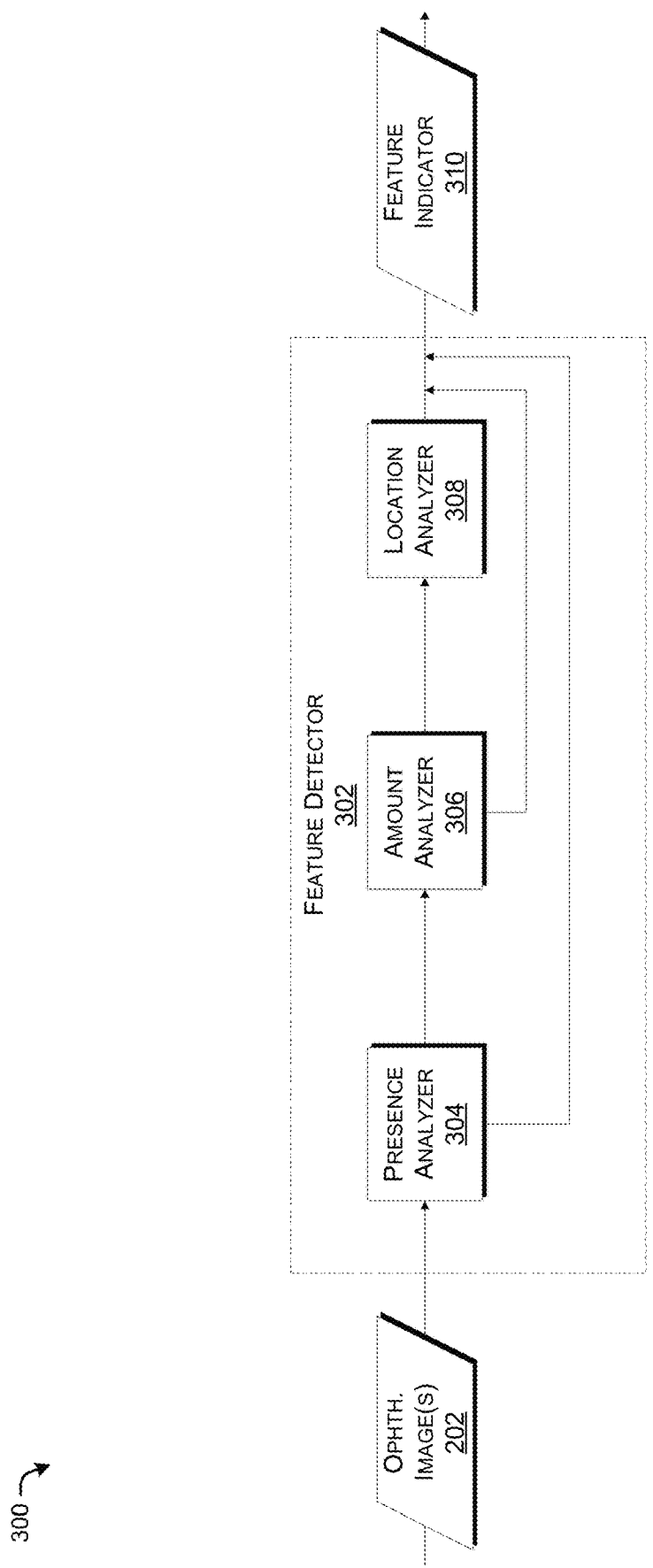
FIG. 3 illustrates an example environment of an implementation of a feature detector.

FIG. 3 illustrates an example environment 300 of an implementation of a feature detector 302, such as any of the feature detectors 208-1 to 208-n described above with reference to FIG. 2. In particular cases, the feature detector 302 includes a presence analyzer 304 that receives the ophthalmic image(s) 202. The presence analyzer 304 may be configured to identify the presence or absence of a type of feature in the ophthalmic image(s).

According to various implementations, a location analyzer 306 may be further configured to analyze the ophthalmic image(s) 202. In some cases, the location analyzer 306 may be configured to identify a location of each feature detected in the ophthalmic image(s) 202. For example, the location analyzer 306 may be configured to determine that a feature is located in a particular quadrant of the eye(s). In some examples, the location analyzer 306 is further configured to identify at least one landmark of the eye(s) depicted in the ophthalmic image(s) 202. In some instances, the location analyzer 306 is configured to identify a distance between an identified feature and an identified landmark.

In some cases in which the type of feature is present in the ophthalmic image(s) 202, an amount analyzer 308 may analyze the ophthalmic image(s) 202. The amount analyzer 308 may be configured to identify a number of the type of feature present in the eye(s) depicted in the ophthalmic image(s) 202. Further, the amount analyzer 308 may be configured to identify a size and/or shape of an individual instance (e.g., each instance) of a feature that is presence in the eye(s) depicted in the ophthalmic image(s) 202. In some cases, the amount analyzer 308 segments pixels depicting the feature from other pixels in the ophthalmic image(s) 202 and identifies the size and/or shape of the feature based on the segmented pixels.

In some cases, the presence analyzer 304, the location analyzer 306, and the amount analyzer 308 can include one or more computing models. For example, the presence analyzer 304 may include at least one first ML model, the location analyzer 306 may include at least one second ML model, and the amount analyzer 308 can include at least one third ML model. In other instances, the presence analyzer 304, location analyzer 306, and the amount analyzer 308 may include a single ML model. Examples of ML models that can be used to implement the presence analyzer 304, the location analyzer 306, the amount analyzer 308 include one or more NNs, such as CNNs (e.g., U-Net) and/or transformer-based models. In some cases, the ML models included in the feature detector 302 are supervised, semi-supervised, self-supervised, and/or unsupervised.

In various cases, the feature detector 302 may be configured to generate a feature indicator 310 based on the determinations and/or identifications made by the presence analyzer 304, the location analyzer 306, and/or the amount analyzer 308. The feature indicator 310 may be output by the feature detector 302 for further analysis. For example, the feature indicator 310 may be output to an evaluator configured to determine whether the ophthalmic image(s) 202 depict one or more diseases based on the feature indicator 310.

Figure 4:
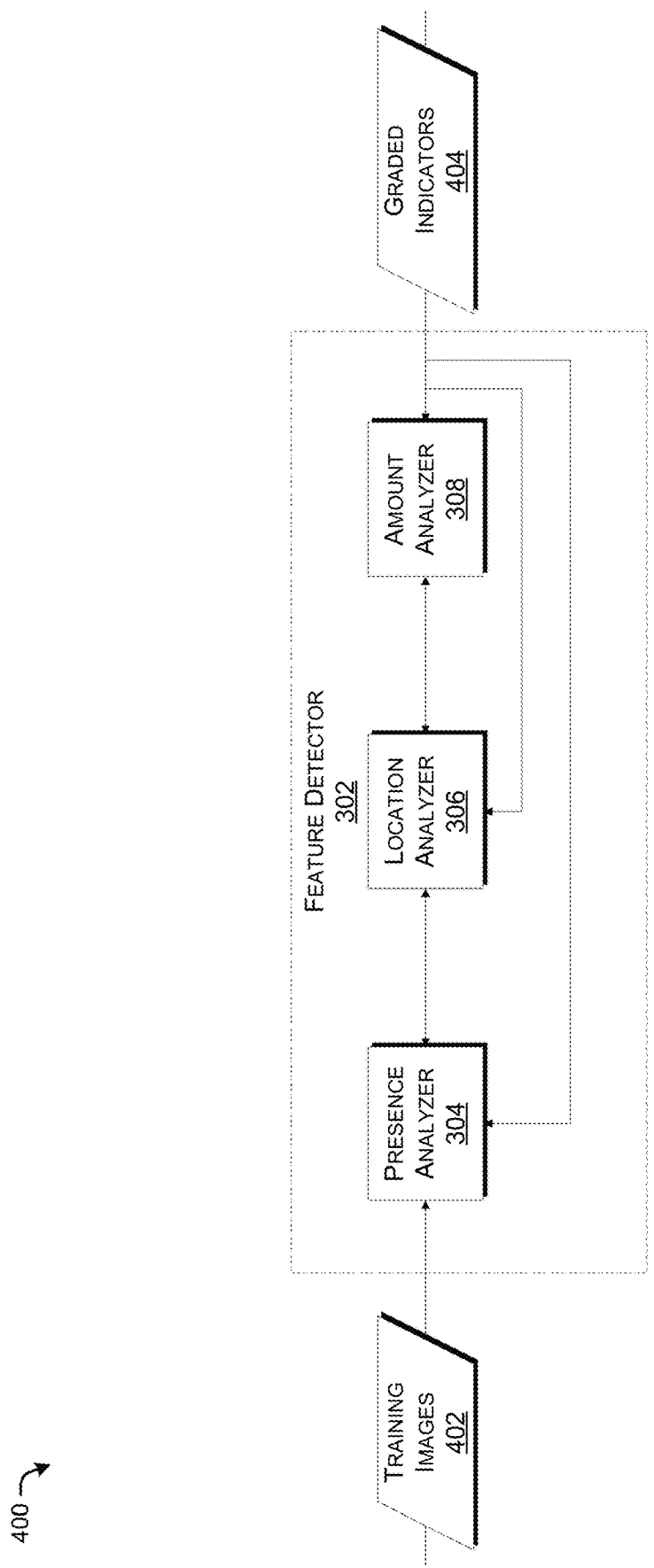
FIG. 4 illustrates an example environment for training a feature detector.

FIG. 4 illustrates an example environment 400 for training the feature detector 302 described above with reference to FIG. 3. As discussed above, the feature detector 302 may include one or more ML models. For example, the presence analyzer 304 may include at least one first ML model, the location analyzer 306 may include at least one second ML model, and the amount analyzer 308 may include at least one third ML model.

Each ML model within the feature detector 302 may include one or more (e.g., multiple) parameters. An individual ML model may receive input data, analyze the input data based on the parameter(s) of the ML model, and generate output data based on the analysis. For instance, a CNN may receive an image as input data, perform one or more convolutions and/or cross-correlation operations on the image with image filters defined by the parameter(s), and generate output data based on the convolved and/or cross-correlated image data. In some cases, an example ML model may further perform a thresholding operation that applies a threshold indicated by the parameter(s) of the ML model.

The parameter(s) of the ML model(s) within the feature detector 302 may be optimized during training. As shown, the feature detector 302 may receive training images 402 as well as graded indicators 404 (or other learning objectives). The training images 402 may depict eyes of a variety of different subjects. The eyes may include eyes depicting the feature to be recognized by the feature detector 302, as well as eyes that do not depict the feature to be recognized by the feature detector 302. For example, the training images 402 may include OCT images, slit lamp images, fundus images, and/or retinal images of multiple subjects in a population.

The graded indicators 404 may indicate the presence of the feature to be detected in the training images 402 and/or specific landmarks in the training images 402. For example, an example graded indicator 404 may indicate the presence or absence of the feature in a corresponding example training image 402. In some cases, an example graded indicator 404 includes a mask indicating a region of pixels depicting the feature in a corresponding example training image 402. For instance, the example graded indicator 404 may include a binary image having the same pixel dimensions as the example training image 402, wherein one pixel value of the binary image indicates pixels in the example training image 402 that are representative of the feature, and the other pixel value of the binary image indicates pixels in the example training image 402 that omit the feature. In some cases, the graded indicators 404 are generated manually by expert graders, such as optometrists, ophthalmologists, or some other type of expert in ophthalmic diagnosis.

Any of a variety of learning types can be applied for training the ML models of the feature detector 302. In an image-based learning type, an ML model can be trained to learn features related to the classification of an entire image. Examples of suitable ML models for image-based learning could be ViT, Swin Transformer, Squeeze and Excitation Network (SENet) (Hue et al., arXiv:1709.01507v4 [cs.CV] 16 May 2019), NFNet (Broch et al., arXiv:2102.06171v1 [cs.CV] 11 Feb. 2021), Resnet (He et al., arXiv: 1512.03385v1 [cs.CV] 10 Dec. 2015), EfficientNet (Tan et al., arXiv:1905.11946v5 [cs.LG] 11 Sep. 2020), VGG (Simonyan et al., arXiv:1905.11946v5 [cs.LG] 11 Sep. 2020), and Alexnet (Krizhevsky et al., COMMUNICATIONS OF THE ACM, May 2017). For example, image-based ML models may be suitable for detecting diseases such as AMD, DR (e.g., and associated severity levels, such as moderate DR or PDR). If the prediction probability is high, features identified using image-based ML models could be used to narrow down the scope of finding individual features within an image. For example, the image-based ML models may be suitable for the presence analyzer 304.

In an object-based learning type, an ML model can be trained to learn to understand how to identify an object (e.g., a defined feature of any shape) within an image. In a patch-based learning type (also referred to as a sub-image- or region-based learning type), an ML model can be trained to identify an object with respect to its shape, type, or relationship to a landmark (e.g., an anatomic structure). This learning type may be used to train the ML model to understand what is within a patch within an image. In a pixel-based learning type, an ML model can be trained to classify individual pixels as belonging to a feature or not belonging to a feature within an image.

For many features, (such as MA, exudates, hemorrhage, cotton-wool spots, IRMA, NVE, NVD) ML models such as U-net (Ronneberger et al., arXiv:1505.04597v1 [cs.CV] 18 May 2015), Faster R-CNN (Ren et al., arXiv:1506.01497v3 [cs.CV] 6 Jan. 2016), Mask R-CNN (He et al., arXiv: 1703.06870v3 [cs.CV] 24 Jan. 2018), or DETR (Canon et al., arXiv:2005.12872v3 [cs.CV] 28 May 2020) and their variants may be suitable for identification. Transformer-based models, such as Swin Transformers, can be used as backbones for these object detection ML models, instead of CNNs. In various implementations, the graded indicators 404 may include regions of the training images 402 corresponding to the graded feature in the regions of the training images 402.

For rare features, such as Roth spots and venous loop, samples of these features 402 can be combined together for training. Features can be further stratified during training as samples of the training images 402 and the graded indicators 404 increase in number. Unsupervised and/or semi-supervised ML models, such as SimCLR-v2 (see, e.g., Chen et al., arXiv:2006.10029v2 [cs.LG] 26 Oct. 2020), or transformer-based approaches (see, e.g., Carton et al., arXiv: 2005.12872v3 [cs.CV] 28 May 2020; ViT; Swin Transformers, etc.) may be used to identify features of sub-images with features, and labeled samples (e.g., the graded indicators 404) may be used to fine-tune the models.

In some examples, the presence analyzer 304 includes a ML model that performs normality filtering. This could be done by using image-based classification and/or feature based algorithms. A number of images that cover abnormal pathologies including those similar to normal ones, such as glaucoma cases, images with subtle MA etc., may be included in the training images 402. The training images 402 may be evaluated via a quality assessment that detects and/or excludes samples from the training images 402 with dirty lens and artifacts. Some normal signs such as Nevus may be included in the training images 402 that depict non-diseased eyes.

Various ML models can be included in the location analyzer 306 for detecting landmarks. In some examples, ML models such as U-Net, Mask R-CNN, DETR, Swin Transformers, and their variants or other object-detection models can be suitable for detecting landmarks, such as OD and fundus. In some cases, a single, integrated ML model detects both OD and fundus. Due to the physiological relationship between OD and fundus, the integrated ML model may have enhanced detection accuracy.

The graded indicators 404 may be input to each one of the presence analyzer 304, the location analyzer 306, and the amount analyzer 308, individually. Similarly, the training images 402 may be input to each one of the presence analyzer 304, the location analyzer 306, and the amount analyzer 308 individually. The feature detector 302 may modify the parameter(s) of the presence analyzer 304, the location analyzer 306, and the amount analyzer 308 based on the training images 402 and the graded indicators 404. In particular, the parameter(s) are optimized such that the presence indicator 304, the location analyzer 306, and the amount analyzer 308 accurately output the graded indicators 404 based on being input with the training images 402.

Once the parameter(s) are optimized and the feature detector 302 is trained, the feature detector 302 may be configured to identify the feature in a new ophthalmic image that is input to the feature detector 302, wherein the new ophthalmic image is not one of the training images 402. Further, once trained, the feature detector 302 may be configured to output a feature indicator based on the new ophthalmic image.

Figure 5:
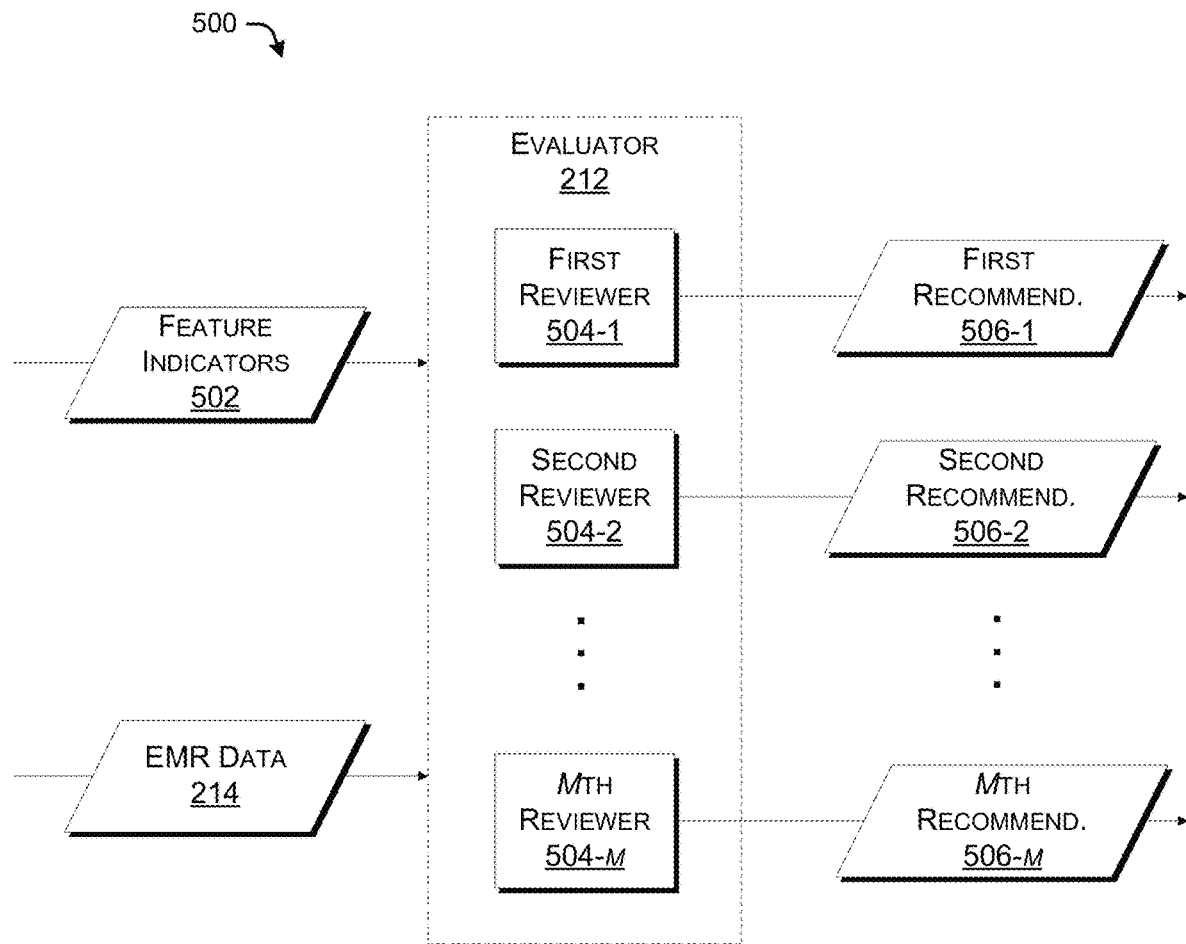
FIG. 5 illustrates an example environment for determining whether a patient is exhibiting one or more diseases based on identified features in at least one eye of the patient.

FIG. 5 illustrates an example environment 500 for determining whether a patient is exhibiting one or more diseases based on identified features in at least one eye of the patient. As shown, the environment 500 includes the evaluator 212 and the EMR data 214 described above with reference to FIG. 2. The evaluator 212 may receive multiple feature indicators 502 that are indicative of multiple identified features in at least one ophthalmic image of a patient.

The evaluator 212 may include first through mth reviewers 504-1 to 504-*m*, wherein m is a positive integer. In various implementations, each of the first through mth reviewers 504-1 to 504-*m* is configured to identify whether the patient is exhibiting one or more diseases. Further, in some cases, each of the first through mth reviewers 504-1 to 504-*m* is configured to identify a severity of at least one disease that is exhibited by the patient. In some implementations, each of the first through mth reviewers 504-1 to 504-*m* is configured to determine whether a referral, further diagnostic step, and/or a treatment is indicated for the identified disease(s). The first through mth reviewers 504-1 to 504-*m* are configured to output first through mth recommendations 506-1 to 506-*m*, respectively, based on the determinations made by the first through mth reviewers 504-1 to 504-*m*.

In some implementations, each of the first through mth reviewers 504-1 to 504-*m* makes its determinations based on a different standard of practice. For example, different medical systems, countries, regions, and professions have different standards of practice for diagnosing diseases and disease severity. In various cases, the first recommendation 506-1 may be in accordance with a first standard of practice, the second recommendation 506-2 may be in accordance with a second standard of practice, and the mth recommendation 506-*m* may be in accordance with an mth standard of practice. However, each one of the first through mth reviewers 504-1 to 504-*m* may rely on the same feature indicators 504 and EMR data 214 to make its determination. Accordingly, the evaluator 212 may evaluate patients in accordance with different standards of practice without retraining any computing models (e.g., ML models) used to identify the features.

In some examples, the first through mth reviewers 504-1 to 504-*m* may include respective computing models. For instance, each one of the first through mth reviewers 504-1 to 504-*m* may include a look-up table indicating correlations between identified features and various diseases in accordance with a particular standard of practice. In some cases, each one of the first through mth reviewers 504-1 to 504-*m* may include a ML model indicating the correlations. For example, the ML model may include a random forest configured to identify a probability of different diseases based on the identified features.

Figure 6:
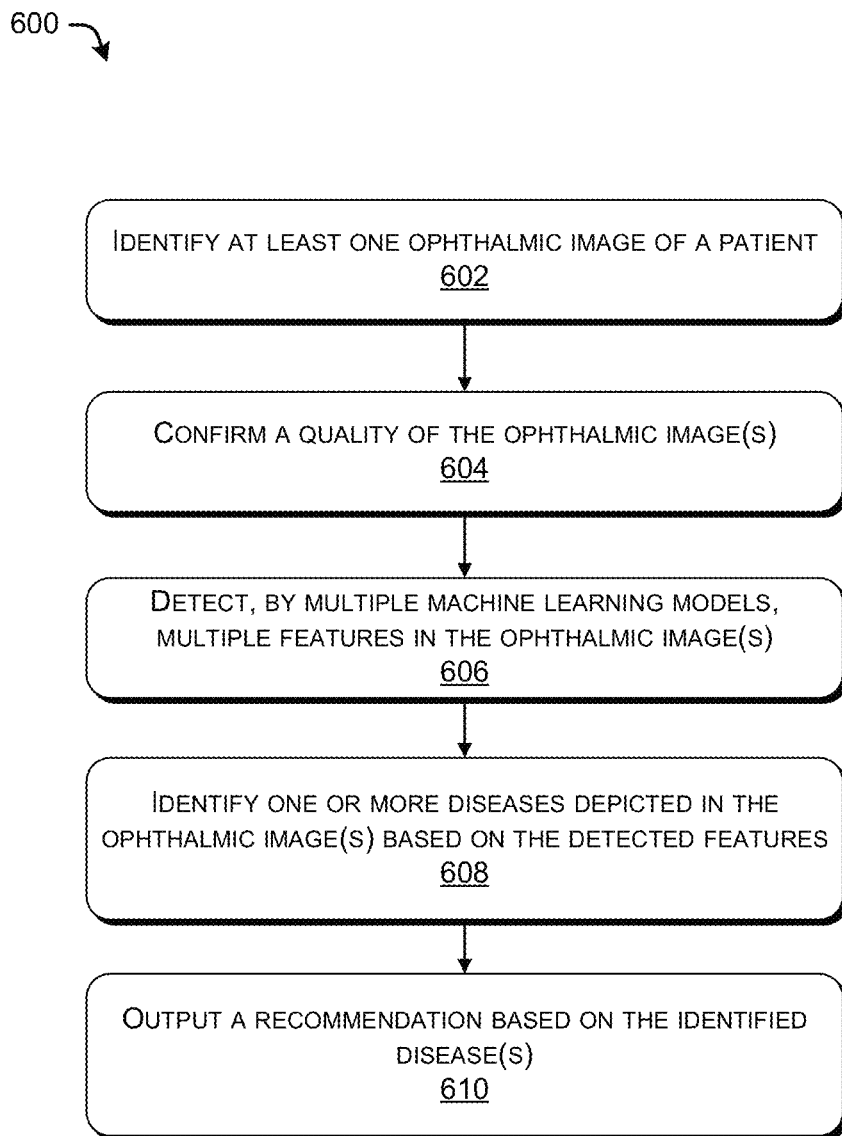
FIG. 6 illustrates an example process for outputting a recommendation in accordance with one or more diseases identified based on one or more ophthalmic images of a patient.

FIG. 6 illustrates an example process 600 for outputting a recommendation in accordance with one or more diseases identified based on one or more ophthalmic images of a patient. The process 600 may be performed by an entity that includes at least one processor and/or may be stored in memory. In some examples, the process 600 may be performed by an entity that includes the image analysis system 112 described above with reference to FIGS. 1 and 2.

At 602, the entity identifies at least one ophthalmic image of a patient. The image(s), for example, may include one or more of an optical coherence tomography (OCT) image, a slit lamp image, a fundus image, or a retinal image. In some examples, the entity includes a medical imaging device configured to obtain the ophthalmic image(s). In some cases, the entity receives the ophthalmic image(s) from a medical imaging device.

At 604, the entity confirms a quality of the ophthalmic image(s). For example, the entity may calculate the quality of the ophthalmic image(s) based on a blurriness of the ophthalmic image(s), blocking in the ophthalmic image(s), ringing in the ophthalmic image(s), image sharpness of the ophthalmic image(s), noise (e.g., white noise) in the ophthalmic image(s), a dynamic range of the ophthalmic image(s), contrast in the ophthalmic image(s), color in the ophthalmic image(s), distortion in the ophthalmic image(s), vignetting in the ophthalmic image(s), LCA in the ophthalmic image(s), artifacts in the ophthalmic image(s), any other qualities that impact the accuracy of ophthalmic structures depicted in the ophthalmic image(s), or any combination thereof. For example, the entity may perform an objective, no-reference technique for identifying the image quality of ophthalmic image(s). In some cases, the entity compares the quality of the ophthalmic image(s) 202 to a threshold. For instance, the entity may determine that the quality of the ophthalmic image(s) 202 is greater than or equal to the threshold.

At 606, the entity detects, by multiple ML models, multiple features in the ophthalmic image(s). In some cases, each ML model may be configured to identify a single type of feature in the ophthalmic image(s). For instance, an example ML model may identify the presence, location, amount, size, and/or shape of a particular feature in the ophthalmic image(s). The multiple ML models, in some examples, may include CNNs, unsupervised ML models, semi-supervised ML models, supervised ML models, or any combination thereof. The features may include multiple features selected from a group of a microaneurysm, a hemorrhage, drusen, exudate, edema, a cup/disc ratio (CDR), focal arteriolar narrowing, arterio-venous nicking, a cotton wool spot, an embolus, a red spot, retinal whitening, a Hollenhorst plaque, a Roth spot, a microinfarct, coagulated fibrin, new vessels elsewhere (NVE), a vitreous hemorrhage (VH), a pre-retinal hemorrhage (PRH), new vessels on a disc (NVD), venous beading, or an intraretinal microvascular abnormality (IRMA).

According to some examples, the entity may determine a proximity of a feature to a landmark within the ophthalmic image(s). For instance, the entity may include a ML model configured to identify at least one of a macula, an optic disc (OD), or a fovea. The entity may further determine a proximity (e.g., physical relationship, such as a distance) between the landmark and a detected feature.

At 608, the entity identifies one or more diseases depicted in the ophthalmic image(s) based on the detected features. In some examples, the entity further identifies the disease(s) based on EMR data associated with the patient whose eye(s) are depicted in the ophthalmic image(s). The diseases, for instance, may include at least two of diabetic retinopathy (DR), age-related macular degeneration (AMD), diabetic macula edema (DME), retinal vein occlusion (RVO), retinopathy of prematurity (ROP), coronary microvascular dysfunction, hypertensive retinopathy, ischemic optic neuropathy, papilledema, retinal artery occlusion, carotid artery occlusion, human immunodeficiency virus (HIV), acquired immunodeficiency syndrome (AIDS), syphilis, malaria, chicken pox, Lyme disease, leukemia, subacute bacterial endocarditis, sepsis, anemia, or any combination thereof.

In some examples, the entity identifies the disease(s) using a different computing model than the computing models used to identify the features. In some cases, the entity identifies the disease(s) using one or more look-up tables. Further, the entity may identify the disease(s) as defined according to multiple standards of practice. The entity may identify a likelihood and/or severity of each disease based on the EMR data and/or the features identified in the ophthalmic image(s).

At 610, the entity outputs a recommendation based on the identified disease(s). The recommendation, for example, may indicate at least one likelihood of the disease(s). In some implementations, the recommendation may indicate the disease(s) corresponding to a likelihood that exceeds a threshold. In particular cases, recommendation may indicate that a referral to a specialist is warranted, based on the identified disease(s). In some examples, the recommendation may indicate one or more treatments (e.g., nutritional recommendations, medications, etc.) associated with treating the identified disease(s).

Figure 7:
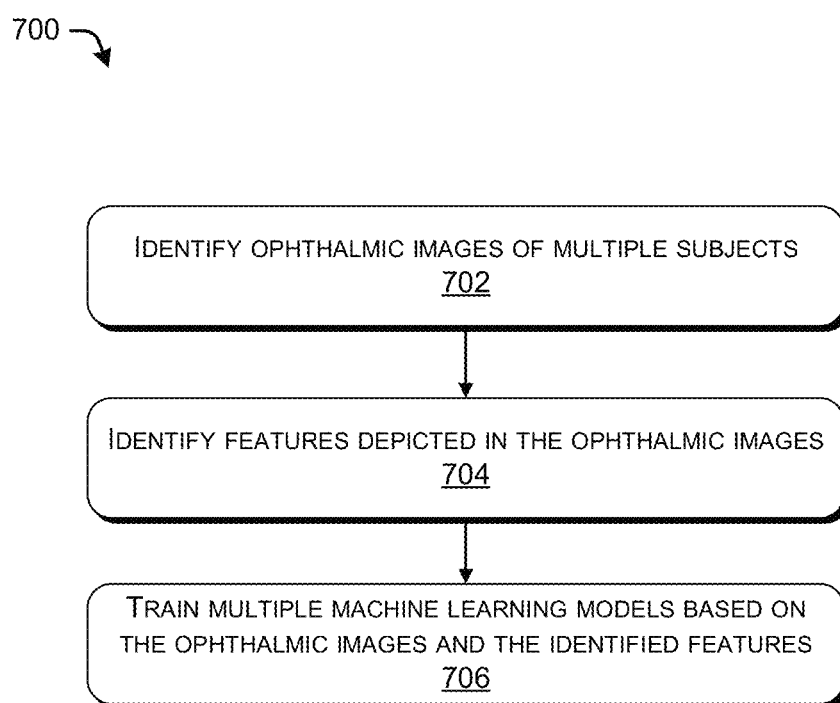
FIG. 7 illustrates an example process for training an image analysis system. The process may be performed by an entity that includes at least one processor and/or may be stored in memory.

FIG. 7 illustrates an example process 700 for training an image analysis system. The process 700 may be performed by an entity that includes at least one processor and/or may be stored in memory. In some examples, the process 700 may be performed by an entity that includes the image analysis system 112 described above with reference to FIGS. 1 and 2.

At 702, the entity may identify ophthalmic images of multiple subjects. The images, for example, may include one or more of OCT images, slit lamp images, fundus images, or retinal images. In some examples, the entity includes one or more medical imaging devices configured to obtain the ophthalmic images. In some cases, the entity receives the ophthalmic image(s) from one or more medical images.

At 704, the entity may identify features depicted in the ophthalmic images. The features may include multiple features selected from a group of a microaneurysm, a hemorrhage, drusen, exudate, edema, a cup/disc ratio (CDR), focal arteriolar narrowing, arterio-venous nicking, a cotton wool spot, an embolus, a red spot, retinal whitening, a Hollenhorst plaque, a Roth spot, a microinfarct, coagulated fibrin, new vessels elsewhere (NVE), a vitreous hemorrhage (VH), a pre-retinal hemorrhage (PRH), new vessels on a disc (NVD), venous beading, or an intraretinal microvascular abnormality (IRMA). In some examples, one or more skilled graders may identify the features and provide inputs to the entity indicating the identified features. For example, the graders may manually segment features within the ophthalmic images. According to some examples, the entity may identify landmarks within the ophthalmic images. For instance, the manual graders may further identify at least one of a macula, an optic disc (OD), or a fovea in each of multiple images.

At 706, the entity may train multiple ML models based on the ophthalmic images and the identified features. Each ML model, for example, may include one or more NNs (e.g., CNNs). During operation, an example NN may receive an image input (e.g., an ophthalmic image) and may provide an output (e.g., the ophthalmic image segmented according to feature). In some examples, the entity may train a CNN by optimizing the parameter(s) based on the ophthalmic images and the identified features. For instance, the entity may perform backprojection to define the parameter(s) of each CNN in the ML models based on the ophthalmic images and the identified features. In some examples, individual ML models may respectively correspond to the features. In some examples, at least one of the ML models may be trained to identify one or more landmarks in ophthalmic images based on the identified landmarks in the multiple images.

Figure 8:
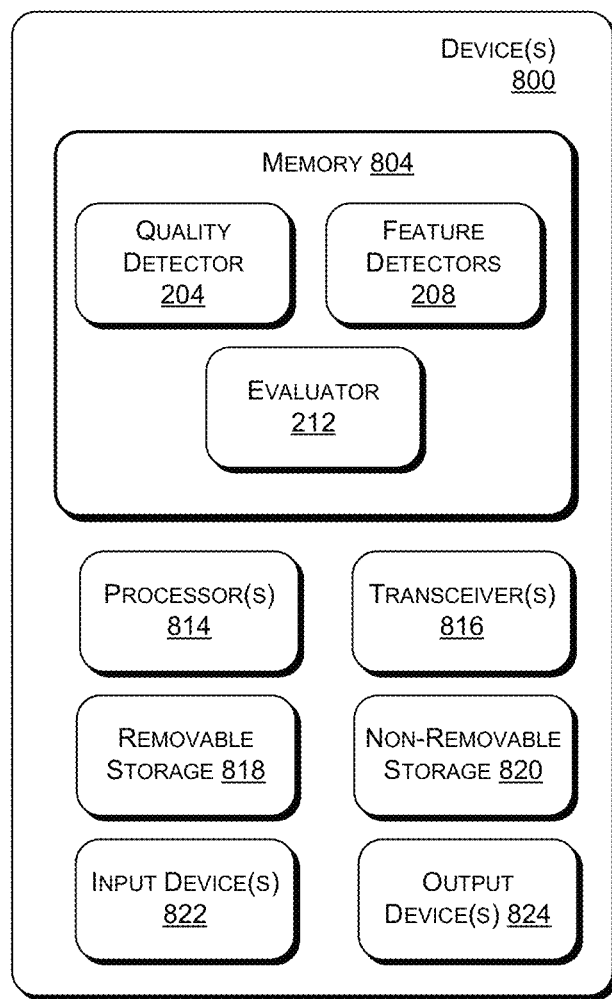
FIG. 8 illustrates at least one example device configured to enable and/or perform the some or all of the functionality discussed herein.

FIG. 8 illustrates at least one example device 800 configured to enable and/or perform the some or all of the functionality discussed herein. Further, the device(s) 800 can be implemented as one or more server computers 802, a network element on a dedicated hardware, as a software instance running on a dedicated hardware, or as a virtualized function instantiated on an appropriate platform, such as a cloud infrastructure, and the like. It is to be understood in the context of this disclosure that the device(s) 800 can be implemented as a single device or as a plurality of devices with components and data distributed among them.

As illustrated, the device(s) 800 comprise a memory 804. In various embodiments, the memory 804 is volatile (including a component such as Random Access Memory (RAM)), non-volatile (including a component such as Read Only Memory (ROM), flash memory, etc.) or some combination of the two.

The memory 804 may include various components, such as the quality detector 204, the feature detectors 208, the evaluator 212, and so on. Any of the quality detector 204, the feature detectors 208, the evaluator 212 can comprise methods, threads, processes, applications, or any other sort of executable instructions. The quality detector 204, the feature detectors 208, the evaluator 212 and various other elements stored in the memory 804 can also include files and databases.

The memory 804 may include various instructions (e.g., instructions in the quality detector 204, the feature detectors 208, and/or the evaluator 212), which can be executed by at least one processor 814 to perform operations. In some embodiments, the processor(s) 814 includes a Central Processing Unit (CPU), a Graphics Processing Unit (GPU), or both CPU and GPU, or other processing unit or component known in the art.

The device(s) 800 can also include additional data storage devices (removable and/or non-removable) such as, for example, magnetic disks, optical disks, or tape. Such additional storage is illustrated in FIG. 8 by removable storage 818 and non-removable storage 820. Tangible computer-readable media can include volatile and nonvolatile, removable and non-removable media implemented in any method or technology for storage of information, such as computer readable instructions, data structures, program modules, or other data. The memory 804, removable storage 818, and non-removable storage 820 are all examples of computer-readable storage media. Computer-readable storage media include, but are not limited to, RAM, ROM, EEPROM, flash memory or other memory technology, CD-ROM, Digital Versatile Discs (DVDs), Content-Addressable Memory (CAM), or other optical storage, magnetic cassettes, magnetic tape, magnetic disk storage or other magnetic storage devices, or any other medium which can be used to store the desired information and which can be accessed by the device(s) 800. Any such tangible computer-readable media can be part of the device(s) 800.

The device(s) 800 also can include input device(s) 822, such as a keypad, a cursor control, a touch-sensitive display, voice input device, etc., and output device(s) 824 such as a display, speakers, printers, etc. In some examples, the input device(s) 822 include a medical imaging device, such as the medical imaging device 104 described above with reference to FIG. 1. In particular implementations, a user can provide input to the device(s) 500 via a user interface associated with the input device(s) 822 and/or the output device(s) 824.

As illustrated in FIG. 8, the device(s) 800 can also include one or more wired or wireless transceiver(s) 816. For example, the transceiver(s) 816 can include a Network Interface Card (NIC), a network adapter, a LAN adapter, or a physical, virtual, or logical address to connect to the various base stations or networks contemplated herein, for example, or the various user devices and servers. To increase throughput when exchanging wireless data, the transceiver(s) 816 can utilize Multiple-Input/Multiple-Output (MIMO) technology. The transceiver(s) 816 can include any sort of wireless transceivers capable of engaging in wireless, Radio Frequency (RF) communication. The transceiver(s) 816 can also include other wireless modems, such as a modem for engaging in Wi-Fi, WiMAX, Bluetooth, or infrared communication.

PARTICULAR EXAMPLES

The following examples provide specific scenarios in which an image analysis system identifies the presence of disease-related features in ophthalmic images of different patients. In these examples, the image analysis system identifies suspected diseases of the patients based on the identified features as well as the EMR (e.g., patient histories) of the patients. In various implementations, the outputs of the image analysis system may trigger additional follow-up and confirmation by an ophthalmologist and/or retina specialist for final diagnosis of each patient.

Example 1: First Patient

In example 1, multiple ML models are used to identify the following features: cotton wool, disc edema, dot/blot hemorrhages, dry drusen, flame hemorrhages, neovascularization, tortuous/engorged vessels, and wet drusen. An image analysis system identifies the following based on at least one ophthalmic image of a first patient:

TABLE 6

| Feature | Result |
| --- | --- |
| Cotton Wool | Pass |
| Disc Edema | Pass |
| Dot/Blot Hemorrhages | Fail - mild; quadrant 1 |
| Dry Drusen | Pass |
| Flame Hemorrhages | Pass |
| Neovascularization | Pass |
| Tortuous/Engorged Vessels | Pass |
| Wet Drusen | Pass |

The image analysis system may determine that the patient has diabetic retinopathy, HIV-related retinopathy, or hypertensive retinopathy based on the features identified by the multiple ML models. In various implementations, the image analysis system identifies the type of retinopathy of the first patient by referring to the EMR (e.g., patient history) of the first patient. For example, if the EMR of the patient indicates first patient is diabetic, then the image analysis system may indicate that the first patient has suspected diabetic retinopathy with an ETDRS level of 35C, or Mild NPDR. In some examples in which the EMR indicates that the patient has HIV (and is not diabetic and has no history of hypertension or headaches), the image analysis system may indicate that the patient has suspected HIV retinopathy. In instances in which the EMR indicates that the first patient has headaches and hypertension (but is not diabetic and does not have HIV), the image analysis system may indicate that the patient has suspected hypertensive retinopathy.

Example 2: Second Patient

Using the same ML models described in Example 1, at least one ophthalmic image of a second patient is evaluated by the image analysis system. The system identifies the following features:

TABLE 7

| Feature | Result |
| --- | --- |
| Cotton Wool | Pass |
| Disc Edema | Pass |
| Dot/Blot Hemorrhages | Detected - severe; quadrant 1, 3 |
| Dry Drusen | Pass |
| Flame Hemorrhages | Pass |
| Neovascularization | Pass |
| Tortuous/Engorged Vessels | Detected - Venous beading, quadrant 2, 4 |
| Wet Drusen | Pass |

The image analysis system may determine that the second patient has diabetic retinopathy, HIV-related retinopathy, or hypertensive retinopathy based on the features identified by the multiple ML models. In various implementations, the image analysis system identifies the type of retinopathy of the second patient by referring to the EMR (e.g., patient history) of the second patient. For example, if the EMR of the second patient indicates the second patient is diabetic, then the image analysis system may indicate that the second patient has suspected diabetic retinopathy with an ETDRS level of 47D, or moderately severe NPDR. In instances in which the EMR of the second patient indicates that the second patient has HIV, the image analysis system may indicate that the second patient has suspected HIV retinopathy. In examples in which the EMR of the second patient indicates the patient has headaches and hypertension, the image analysis system may indicate that the second patient has suspected hypertensive retinopathy.

Example 3: Third Patient

Using the same ML models described in Example 1, at least one ophthalmic image of a third patient is evaluated by the image analysis system. The system identifies the following features:

TABLE 8

| Feature | Result |
| --- | --- |
| Cotton Wool | Pass |
| Disc Edema | Pass |
| Dot/Blot Hemorrhages | Detected - severe; quadrant 1, 3 |
| Dry Drusen | Pass |
| Flame Hemorrhages | Pass |
| Neovascularization | Pass |
| Tortuous/Engorged Vessels | Detected - Venous beading, quadrant 2, 4 |
| Wet Drusen | Detected - Medium drusen |

The image analysis system may determine that the third patient has diabetic retinopathy, HIV-related retinopathy, or hypertensive retinopathy based on the features identified by the multiple ML models. In various implementations, the image analysis system identifies the type of retinopathy of the third patient by referring to the EMR (e.g., patient history) of the third patient. In examples in which the EMR of the third patient indicates that the third patient is over 55 and diabetic, the image analysis system may indicate that the third patient has suspected diabetic retinopathy with an ETDRS level of 47D, or moderately severe NPDR. Further, the image analysis system may indicate that, in accordance with National Institute for Health and Care Excellence (NICE) guidelines for age-related macular degeneration diagnosis, the third patient has a suspected AMD grade 2/mild. Overall, the image analysis system may indicate that the third patient is suspected to have moderately severe NPDR, AMD grade 2.

In examples in which the EMR of the third patient indicates that the patient is not over 55, but is diabetic, the image analysis system may indicate that the third patient is suspected to have an ETDRS level of 47D, or moderately severe NPDR (with drusen), but is not suspected to have AMD (because a patient is under 55 so it is very unlikely to have AMD).

In examples in which the EMR of the third patient indicates the third patient is over 55 and has HIV, the image analysis system may indicate that the third patient is suspected to have HIV retinopathy, AMD Grade 2

CONCLUSION

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

As used herein, the term "based on" can be used synonymously with "based, at least in part, on" and "based at least partly on."

As used herein, the terms "comprises/comprising/comprised" and "includes/including/included," and their equivalents, can be used interchangeably. An apparatus, system, or method that "comprises A, B, and C" includes A, B, and C, but also can include other components (e.g., D) as well. That is, the apparatus, system, or method is not limited to components A, B, and C.

Furthermore, numerous references have been made to printed publications, journal articles and other written text throughout this specification (referenced materials herein). Each of the referenced materials are individually incorporated herein by reference in their entirety for their referenced teaching.

The Appendix of this application describes various illustrative examples related to implementations of the present disclosure. The Appendix is not intended to limit the scope of the disclosure, or the claims, in any manner.

Although the subject matter has been described in language specific to structural features and/or methodological acts, it is to be understood that the subject matter defined in the appended claims is not necessarily limited to the specific features or acts described.

The invention claimed is:

1. A system comprising:
   a medical imaging device configured to generate at least one image of at least one eye of a patient;
   at least one processor communicatively coupled to the medical imaging device; and
   memory storing instructions that, when executed by the at least one processor, cause the at least one processor to perform operations comprising:
      detecting, by at least one trained machine learning (ML) model, a set of features in an image of an eye of a patient;
      determining, based on a first subset of features included in the set of features, whether the patient exhibits a first disease of multiple diseases;
      determining, based on a second subset of features included in the set of features, whether the patient exhibits a second disease of the multiple diseases; and generating a recommendation for care of the patient based on whether the patient exhibits the first disease or the second disease; and an output device configured to output the recommendation.

2. The system of claim 1, wherein the at least one image comprises one or more of an optical coherence tomography (OCT) image, a slit lamp image, a fundus image, a fluorescence angiogram, a color fundus photography (CFP) image, a fluorescein angiography (FA) image, an indocyanine green (ICG) angiography image, a fundus autofluorescence (FAF) image, or a retinal image.

3. The system of claim 1, wherein the operations further comprise:
determining at least one of a number, a size, a location, or a shape of at least one feature of the first subset of features,
the at least one processor determining whether the patient exhibits the first disease based on the at least one of the number, the size, the location, or the shape of the at least one feature.

4. The system of claim 1, wherein the operations further comprise:
detecting a landmark depicted in the image, the landmark comprising at least one of a macula, an optic disc (OD), or a fovea of the at least one eye; and
determining a distance between at least one feature of the first subset of features and the landmark,
the at least one processor determining whether the patient exhibits the first disease based on the distance between the at least one feature and the landmark.

5. The system of claim 1, wherein:
a first feature of the first subset of features comprises a microaneurysm, a hemorrhage, drusen, exudate, edema, a cup/disc ratio (CDR), focal arteriolar narrowing, arterio-venous nicking, a cotton wool spot, an embolus, a red spot, retinal whitening, a Hollenhorst plaque, a Roth spot, a microinfarct, coagulated fibrin, new vessels elsewhere (NVE), a vitreous hemorrhage (VH), a pre-retinal hemorrhage (PRH), new vessels on a disc (NVD), venous beading, or an intraretinal microvascular abnormality (IRMA), and
a second feature of the second subset of features comprises the microaneurysm, the hemorrhage, the drusen, the exudate, the edema, the CDR, the focal arteriolar narrowing, the arterio-venous nicking, the cotton wool spot, the embolus, the red spot, the retinal whitening, the Hollenhorst plaque, the Roth spot, the microinfarct, the coagulated fibrin, the NVE, the VH, the PRH, the NVD, the venous beading, or the IRMA,
wherein the first feature is different than the second feature.

6. The system of claim 1, wherein:
the at least one trained ML model comprises a set of ML models including at least one of: a first supervised learning model, a first unsupervised learning model, or a first semi-supervised learning model, and
each ML model of the set of ML models is characterized by a same ML architecture.

7. The system of claim 1, wherein:
determining whether the patient exhibits the first disease or the second disease comprises identifying a severity associated with the first disease or the second disease, and
the recommendation is based at least in part on the severity.

8. The system of claim 1, wherein training a ML model, included in the at least one trained ML model, to detect a particular feature is based on a training dataset identifying a set of images depicting the particular feature.

9. The system of claim 1, the operations further comprising:
identifying, based on a region associated with the patient, a standard of practice,
the at least one processor determining whether the patient exhibits the first disease or the second disease based on the standard of practice.

10. The system of claim 9, wherein the recommendation is based on the standard of practice.

11. A system comprising:
at least one processor communicatively coupled to a medical imaging device; and
memory storing instructions that, when executed by the at least one processor, cause the at least one processor to perform operations comprising:
identifying at least one image of an eye of a patient;
detecting, by at least one trained computing model, a set of features in an image of the at least one image;
determining, by a disease computing model separate from the at least one computing models and based on the set of features, one or more likelihoods, each likelihood associated with whether the patient has a disease of multiple diseases; and
generating a recommendation for care of the patient based on the one or more likelihoods.

12. The system of claim 11, wherein the at least one image comprises one or more of an optical coherence tomography (OCT) image, a slit lamp image, a fundus image, a fluorescence angiogram, a color fundus photography (CFP) image, a fluorescein angiography (FA) image, an indocyanine green (ICG) angiography image, a fundus autofluorescence (FAF) image, or a retinal image.

13. The system of claim 11, wherein:
the operations further comprise:
detecting, by a first computing model included in the at least one trained computing model, a landmark depicted in the image, the landmark comprising at least one of a macula, an optic disc (OD), or a fovea the at least one eye; and
determining, by the first computing model, a distance between a respective feature corresponding to the first computing model feature and the landmark,
wherein the one or more likelihoods are determined based on the distance.

14. The system of claim 11, wherein:
a feature of the set of features comprises a microaneurysm, a hemorrhage, drusen, exudate, edema, a cup/disc ratio (CDR), focal arteriolar narrowing, arterio-venous nicking, a cotton wool spot, an embolus, a red spot, retinal whitening, a Hollenhorst plaque, a Roth spot, a microinfarct, coagulated fibrin, new vessels elsewhere (NVE), a vitreous hemorrhage (VH), a pre-retinal hemorrhage (PRH), new vessels on a disc (NVD), venous beading, or an intraretinal microvascular abnormality (IRMA).

15. The system of claim 11, wherein:
the at least one trained computing model comprises a set of ML models including at least one of a supervised learning model, a unsupervised learning model, or a semi-supervised learning model, and
the disease computing model comprises a look-up table.

16. The system of claim 11, wherein:
the operations further comprise identifying data indicative of an electronic medical record (EMR) of the patient,
the at least one processor determining the one or more likelihoods based on the data indicative of the EMR of the patient.

17. The system of claim 11, wherein the multiple diseases include at least one of diabetic retinopathy (DR), age-related macular degeneration (AMD), diabetic macula edema (DME), retinal vein occlusion (RVO), retinopathy of prematurity (ROP), coronary microvascular dysfunction, hypertensive retinopathy, ischemic optic neuropathy, papilledema, retinal artery occlusion, carotid artery occlusion, human immunodeficiency virus (HIV), acquired immunodeficiency syndrome (AIDS), syphilis, malaria, chicken pox, Lyme disease, leukemia, subacute bacterial endocarditis, sepsis, or anemia.

18. A method, comprising:
generating an image of at least one eye of a patient;
detecting, by at least one trained machine learning (ML) model, a set of features in the image;
determining, by a processor, based on a first subset of features included in the set of features, whether the patient exhibits a first disease of multiple diseases;
determining, by the processor and based on a second subset of features included in the set of features, whether the patient exhibits a second disease of the multiple diseases;
generating, by the processor, a recommendation for care of the patient based on whether the patient exhibits the first disease or the second disease; and
providing, by the processor, an output to an output device, the output indicating the recommendation.

19. The method of claim 18, further comprising:
determining at least one of a number, a size, a location, or a shape of at least one feature of the first set of features,
the processor determining the first disease is based on the at least one of the number, the size, the location, or the shape of the at least one first feature.

20. The method of claim 18, further comprising:
detecting a landmark depicted in the image, the landmark comprising at least one of a macula, an optic disc (OD), or a fovea of the at least one eye; and
determining a distance between at least one feature of the first subset of features and the landmark,
the processor determining whether the patient exhibits the first disease based on the distance between the at least one feature and the landmark.

21. A non-transitory computer-readable medium storing instructions which, when executed by a processor, cause the processor to:
receive an image of at least one eye of a patient;
determine, by providing the image as an input to at least one trained machine learning (ML) model, a set of features in the image;
determine, based on a first subset of features included in the set of features, whether the patient exhibits a first disease of multiple diseases;
determine, based on a second subset of features included in the set of features, whether the patient exhibits a second disease of the multiple diseases;
generate a recommendation for care of the patient based on whether the patient exhibits the first disease or the second disease; and
provide an output to an output device, the output indicating the recommendation.

22. The non-transitory computer-readable medium of claim 21, wherein the instructions further cause the processor to:
detect a landmark in the image, the landmark comprising at least one of a macula, an optic disc (OD), or a fovea of the eye;
determine a distance between at least one feature of the first subset of features and the landmark,
the processor determining whether the patient exhibits the first disease based on the distance between the at least one feature and the landmark.

23. The non-transitory computer-readable medium of claim 21, wherein training a first ML model included in the at least one trained ML model comprises:
identifying first images of eyes of multiple first patients;
identifying first indications of a first feature depicted in a first subset of the first images; and
providing, as a training dataset, the first subset of the first image and the first indications of the first feature,
wherein the first ML model is trained to detect the first feature using the training dataset.

* * * * *